(12) United States Patent
Hultgren et al.

(10) Patent No.: US 10,265,150 B2
(45) Date of Patent: *Apr. 23, 2019

(54) SYSTEM AND METHOD FOR FABRICATING A DENTAL RESTORATION

(71) Applicant: Bruce Willard Hultgren, Victoria, MN (US)

(72) Inventors: Bruce Willard Hultgren, Victoria, MN (US); Steven Mark Rzepecki, Edina, MN (US)

(73) Assignee: BRUCE WILLARD HULTGREN, Victoria, MN (US)

( * ) Notice: Subject to any disclaimer, the term of this patent is extended or adjusted under 35 U.S.C. 154(b) by 1 day.

This patent is subject to a terminal disclaimer.

(21) Appl. No.: 15/835,955

(22) Filed: Dec. 8, 2017

(65) Prior Publication Data

US 2018/0098827 A1    Apr. 12, 2018

Related U.S. Application Data

(63) Continuation of application No. 14/752,389, filed on Jun. 26, 2015, now Pat. No. 9,848,964, which is a (Continued)

(51) Int. Cl.
*A61C 19/05* (2006.01)
*A61B 5/00* (2006.01)
(Continued)

(52) U.S. Cl.
CPC ............ *A61C 19/05* (2013.01); *A61B 5/0088* (2013.01); *A61B 5/1111* (2013.01);
(Continued)

(58) Field of Classification Search
CPC ... A61C 9/004; A61C 9/0053; A61C 13/0004; A61C 19/05
See application file for complete search history.

(56) References Cited

U.S. PATENT DOCUMENTS

| 4,169,314 A | 10/1979 | Mercer et al. |
| 4,859,181 A * | 8/1989 | Neumeyer ............ A61B 5/1114 433/69 |

(Continued)

FOREIGN PATENT DOCUMENTS

WO    02/32340 A2    4/2002

OTHER PUBLICATIONS

PCT International Search Report and Written Opinion in PCT/US2016/039354, dated Sep. 12, 2016, 19 pages.

*Primary Examiner* — Ralph A Lewis
(74) *Attorney, Agent, or Firm* — Merchant & Gould P.C.

(57) ABSTRACT

A system for fabricating a dental restoration to restore a plurality of teeth in a dentition of a patient is described. The dentition includes a restoration dental arch and an opposing dental arch. The restoration dental arch includes a restoration site and the opposing dental arch is opposite the restoration dental arch. The system includes an impression apparatus, a motion capture apparatus, an interference model generation system, and a restoration design system. The impression apparatus is configured to capture an impression of the dentition of the patient. The motion capture apparatus is configured to capture a plurality of location data points that represent the locations of the opposing dental arch relative to the restoration dental arch. The interference model generation system is configured to generate an interference model for the restoration site. The restoration design system is for designing a restoration using the interference model.

7 Claims, 35 Drawing Sheets

Related U.S. Application Data continuation-in-part of application No. 14/695,353, filed on Apr. 24, 2015, now Pat. No. 9,861,458.

(60) Provisional application No. 61/983,888, filed on Apr. 24, 2014.

(51) Int. Cl.

| | | |
|---|---|---|
| *A61C 13/34* | (2006.01) | |
| *A61C 9/00* | (2006.01) | |
| *A61B 5/11* | (2006.01) | |
| *A61K 6/10* | (2006.01) | |
| *G05B 19/4099* | (2006.01) | |
| *A61C 13/00* | (2006.01) | |
| *A61K 6/083* | (2006.01) | |

(52) U.S. Cl.

CPC .......... *A61B 5/1128* (2013.01); *A61B 5/4542* (2013.01); *A61C 9/0006* (2013.01); *A61C 9/0053* (2013.01); *A61C 13/0004* (2013.01); *A61C 13/34* (2013.01); *A61K 6/083* (2013.01); *A61K 6/10* (2013.01); *G05B 19/4099* (2013.01); *A61B 5/0037* (2013.01); *A61C 19/052* (2013.01); *G05B 2219/35044* (2013.01); *G05B 2219/37555* (2013.01); *G05B 2219/45167* (2013.01); *G05B 2219/49008* (2013.01); *Y02P 90/265* (2015.11)

(56) References Cited

U.S. PATENT DOCUMENTS

| | | | |
|---|---|---|---|
| 6,152,731 A | 11/2000 | Jordan | |
| 6,808,659 B2 | 10/2004 | Schulman et al. | |
| 6,915,178 B2 | 7/2005 | O'Brien et al. | |
| 7,118,375 B2 | 10/2006 | Durbin | |
| 7,160,110 B2 * | 1/2007 | Imgrund | A61C 7/00 433/213 |
| 7,824,346 B2 | 11/2010 | Marshall | |
| 8,200,462 B2 | 6/2012 | Marshall et al. | |
| 8,366,445 B2 | 2/2013 | Vuillemot | |
| 8,753,114 B2 | 6/2014 | Vuillemot | |
| 9,125,712 B2 | 9/2015 | Kraemer | |
| 9,848,964 B2 * | 12/2017 | Hultgren | A61C 13/0004 |
| 9,861,458 B2 | 1/2018 | Hultgren | |
| 2005/0042577 A1 | 2/2005 | Kvitrud et al. | |
| 2005/0095562 A1 | 5/2005 | Sporbert et al. | |
| 2009/0068617 A1 | 3/2009 | Lauren | |
| 2009/0148816 A1 | 6/2009 | Marshall et al. | |
| 2011/0008751 A1 | 1/2011 | Pettersson | |
| 2011/0212420 A1 | 9/2011 | Vuillemot | |
| 2012/0291284 A1 | 11/2012 | Warden et al. | |
| 2013/0073265 A1 | 3/2013 | Kraemer et al. | |
| 2013/0130202 A1 | 5/2013 | Vuillemot | |
| 2014/0255877 A1 * | 9/2014 | Schweiger | A61C 9/004 433/214 |
| 2015/0019176 A1 | 1/2015 | Presswood et al. | |
| 2015/0305839 A1 | 10/2015 | Hultgren et al. | |
| 2016/0175076 A1 | 6/2016 | Hultgren et al. | |
| 2018/0110597 A1 | 4/2018 | Hultgren | |

* cited by examiner

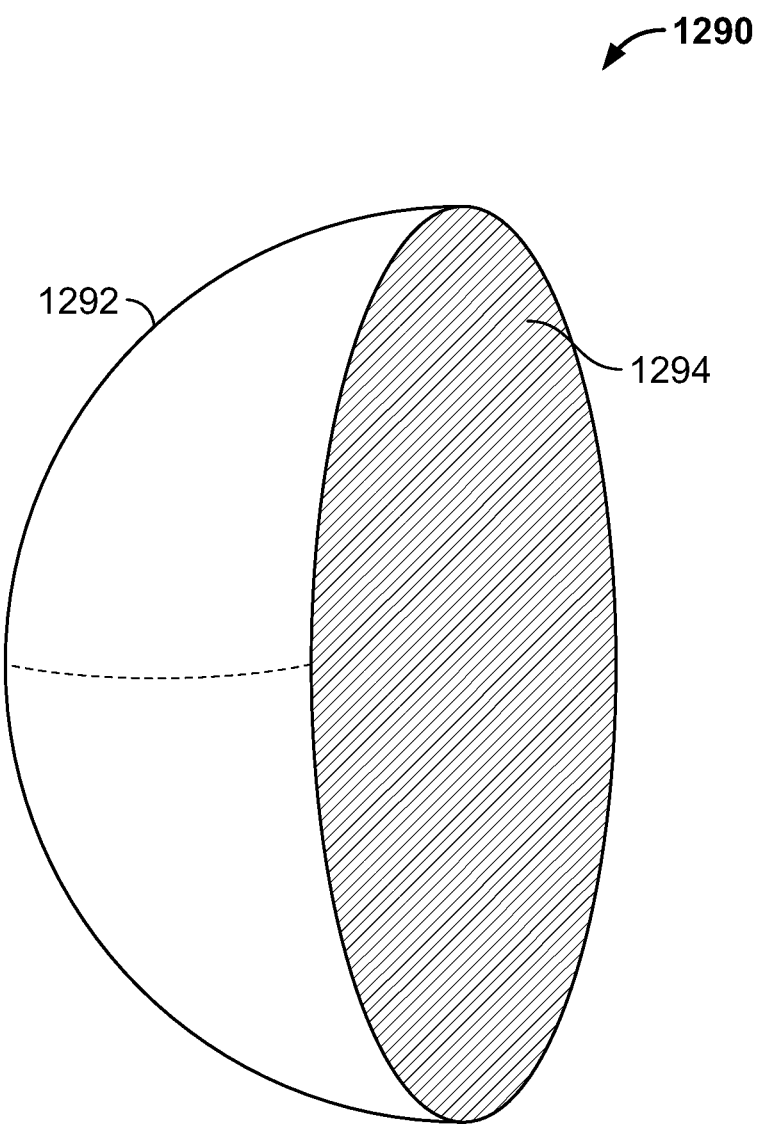
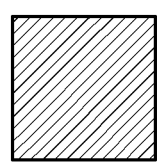 Contoured Surface
FIG. 34

SYSTEM AND METHOD FOR FABRICATING A DENTAL RESTORATION

CROSS REFERENCE TO RELATED APPLICATION(S)

This application is a continuation of U.S. patent application Ser. No. 14/752,389, filed on Jun. 26, 2015, titled SYSTEM AND METHOD FOR FABRICATING A DENTAL RESTORATION, now U.S. Pat. No. 9,848,964, which is a continuation-in-part of U.S. patent application Ser. No. 14/695,353, filed on Apr. 24, 2015, titled SYSTEM AND METHOD FOR FABRICATING A DENTAL RESTORATION, now U.S. Pat. No. 9,861,458, which claims priority to U.S. Patent Application No. 61/983,888, filed on Apr. 24, 2014, titled SYSTEM AND METHOD FOR FABRICATING A DENTAL RESTORATION, the disclosures of which are hereby incorporated by reference in their entirety.

BACKGROUND

Teeth are typically classified as anterior or posterior. Anterior teeth are in the front of the mouth; posterior teeth are in the back of the mouth. Typically, a patient has six upper anterior teeth and six lower anterior teeth. The anterior teeth usually have a narrow incisal edge. In a patient who has a normal bite relationship, the incisal edges of the upper anterior teeth are positioned slightly further towards the front of the patient's mouth than the incisal edges of the lower anterior teeth. In this arrangement, the incisal edge of the lower anterior teeth may contact the rear-facing (or lingual) surface of the upper anterior teeth.

A patient can have as many as ten upper posterior teeth and ten lower posterior teeth, although it is quite common to have fewer (e.g., wisdom teeth are frequently removed). The posterior teeth have an occlusal surface that faces the teeth on the opposite arch and forms the biting surface.

A dental restoration is used to restore a tooth or multiple teeth. For example, a crown is a dental restoration that is used to restore a single tooth. A bridge is another example of a dental restoration. A bridge restores multiple teeth. In some circumstances, dental restorations are used to restore functionality after a tooth is damaged. In other circumstances, dental restorations are used to aesthetically improve a patient's dentition.

Generally, a dental restoration must fit harmoniously with the patient's surrounding dentition, and especially with the opposing dentition. For example, the occlusal surface (i.e., the biting surface) of a restoration should be carefully designed to avoid interfering with the closure and movement of the jaw.

SUMMARY

In general terms, this disclosure is directed to a system and method for simulating occlusal interference using a functional bite map. In one possible configuration and by non-limiting example, a dental restoration is compared to an interference surface generated from a functional bite map to identify occlusal interference regions.

One aspect is a system for fabricating a dental restoration to restore a tooth at a restoration site in a dentition of a patient, wherein the dentition includes a restoration dental arch and an opposing dental arch, the restoration dental arch including the restoration site and the opposing dental arch being opposite the restoration dental arch, comprising: an impression apparatus configured to capture an impression of the dentition of the patient, the portion of the dentition including the restoration site; a motion capture apparatus configured to capture a plurality of location data points, the location data points representing the locations of the opposing dental arch relative to the restoration dental arch as the dentition moves between a plurality of bite positions; an interference model generation system configured to generate an interference model for the restoration site, wherein the interference model includes an interference surface, the interference surface corresponding to the locations of a portion of the opposing dental arch in at least a portion of the plurality of the locations represented by the plurality of location data points; and a restoration design system for designing a restoration using the interference model.

Another aspect is a method of generating a dental restoration for a patient, comprising: generating an interference model from an impression and a functional bite map, the impression representing at least a portion of a dentition of the patient, the functional bite map representing bite registration information for a plurality of positions of the dentition of the patient; aligning the interference model to a restoration site of the patient; and designing a dental restoration for the restoration site using the interference model.

Yet another aspect is a method of generating a dental restoration to restore an anterior tooth of a patient, comprising: generating an incisal guide path, using a computing device, corresponding to the lingual surface of the anterior tooth; fabricating an incisal guide path structure based on the incisal guide path; and using the incisal guide path structure to generate the dental restoration.

Another aspect is a system for fabricating a dental restoration to restore a plurality of teeth in a dentition of a patient, wherein the dentition includes a restoration dental arch and an opposing dental arch, the restoration dental arch including a restoration site and the opposing dental arch being opposite the restoration dental arch, comprising: an impression apparatus configured to capture an impression of the dentition of the patient, the portion of the dentition including the restoration site; a motion capture apparatus configured to capture a plurality of location data points, the location data points representing the locations of the opposing dental arch relative to the restoration dental arch as the dentition moves between a plurality of bite positions; an interference model generation system configured to generate an interference model for the restoration site, wherein the interference model includes an interference surface, the interference surface corresponding to the locations of a portion of the opposing dental arch in at least a portion of the plurality of the locations represented by the plurality of location data points; and a restoration design system for designing a restoration using the interference model.

Yet another aspect is a method of generating a denture dental restoration for a patient, comprising: generating an interference surface from an impression and motion data, the impression representing at least a portion of a dentition of the patient, the motion data representing a plurality of positions of the dentition of the patient; aligning the interference surface to a restoration site of the patient; and designing a dental restoration for the restoration site using the interference surface.

Another aspect is a fiducial device for use in imaging a dentition of a patient, comprising: an exterior surface, wherein the exterior surface is a portion of the surface of a sphere; and an interior surface, wherein the interior surface is contoured to fit a tooth.

BRIEF DESCRIPTION OF THE DRAWINGS

FIG. 34 illustrates an embodiment of a fiducial device that can be secured to a portion of the dentition of the patient for use in generating the motion data of FIG. 1.

DETAILED DESCRIPTION

Figure 1:
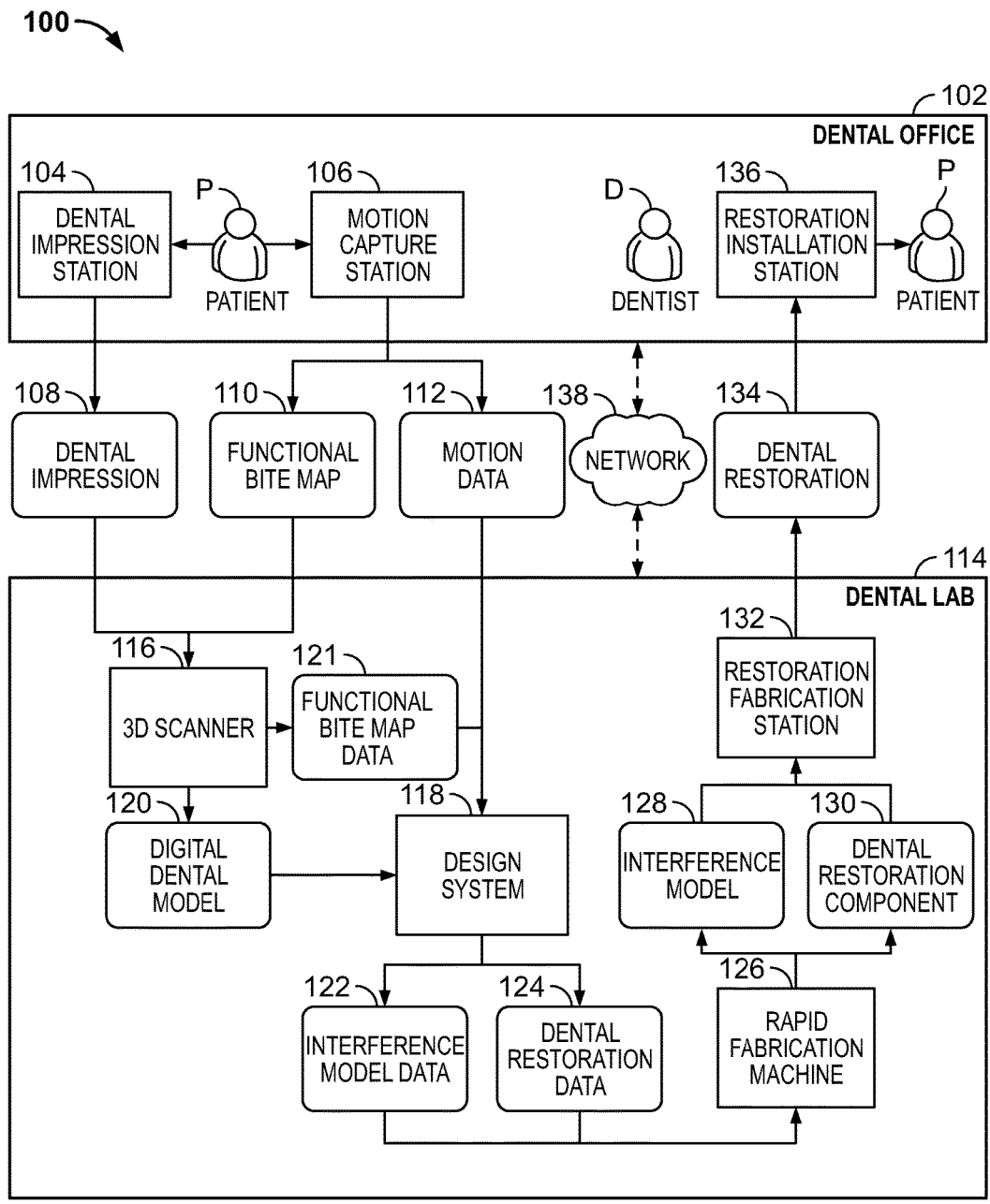
FIG. 1 is a schematic block diagram illustrating an example of a system for simulating occlusal interference using a functional bite map.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The present disclosure relates to a system for fabricating dental restorations. The dental restoration is configured to temporarily or permanently replace part or all of one or more of a patient's teeth. In some embodiments, the dental restorations are fabricated to avoid interfering with the opposing dentition. In some embodiments, relative motion data is used to construct an interference model representative of the position of the opposing dentition in multiple bite locations. In some embodiments, a mold is fabricated based on an incisal guide plane. In some embodiments, the mold is used to fabricate the restoration. In some embodiments, the incisal guide plane is generated from motion data. In other embodiments, the incisal guide plane is generated from an impression of the dentition of a patient.

FIG. 1 is a schematic block diagram illustrating an example of a system 100 for simulating occlusal interference using a functional bite map to fabricate a dental restoration 134. In this example, the system 100 includes a dental office 102 and a dental lab 114.

The example dental office 102 includes a dental impression station 104, a motion capture station 106, and a restoration installation station 136. Although shown as a single dental office in this figure, in some embodiments, the dental office 102 comprises multiple dental offices. For example, in some embodiments, one or both of the dental impression station 104 and the motion capture station 106 are in a different dental office than the restoration installation station 136. Further, in some embodiments, one or more of the dental impression station 104, the motion capture station 106, and the restoration installation station 136 are not in a dental office.

The example dental impression station 104 generates a dental impression 108 of the dentition of the patient P. The dental impression 108 is a geometric representation of the dentition of the patient P. In some embodiments, the dental impression 108 is a physical impression captured using an impression material, such as sodium alginate, or vinyl polysiloxane. In other embodiments, other impression materials are used as well.

In some embodiments, the dental impression 108 is a digital impression. In some embodiments, the digital impression is represented by one or more of a point cloud, a polygonal mesh, a parametric model, or voxel data. In some embodiments, the digital impression is generated directly from the dentition of the patient P, using for example an intraoral scanner. Example intraoral scanners include the TRIOS Intra Oral Digital Scanner, the Lava Chairside Oral Scanner C.O.S., the Cadent iTero, the Cerec AC, the Cyrtina IntraOral Scanner, and the Lythos Digital Impression System from Ormco. In other embodiments, a digital impression is captured using other imaging technologies, such as computed tomography (CT), including cone beam computed tomography (CBCT), ultrasound, and magnetic resonance imaging (MRI). In yet other embodiments, the digital impression is generated from a physical impression by scanning the impression or plaster model of the dentition of the patient P created from the physical impression. Examples of technologies for scanning a physical impression or model include three dimensional laser scanners and computed tomography (CT) scanners. In yet other embodiments, digital impressions are created using other technologies.

The motion capture station 106 captures a representation of the movement of the dental arches relative to each other. In some embodiments, the motion capture station generates at least one of a functional bite map 110 and motion data 112.

In some embodiments, the functional bite map 110 is a physical apparatus containing indentations that form a path that corresponds to the movement of the dental arches of the patient relative to each other. For example, in some embodiments, the functional bite map 110 is formed in one or more sheets of a bite registration material. In some embodiments, the patient P bites into the bite registration material. In some embodiments, after the patient P bites into the bite registration material, the patient P is instructed to move between various bite positions, such as such as centric, excursive, left lateral, and right lateral. In other embodiments, the functional bite map 110 is formed from multiple sheets of bite registration material that are each captured in a different bite position. In some embodiments, the bite registration material is formed from wax, alginate, vinyl polysiloxane, or combinations thereof. In some embodiments, the bite registration material is formed from wax infused with a powdered metal, such as aluminum or copper. Some example bite registration materials include THEMACRYL® thermoplastic material from Airway Technologies, LLC of Carrollton, Tex.; vinyl polysiloxane putty such as FLEXITIME® impression material from Heraeus Kulzer of South Bend, Ind.; FUTAR® D bite registration material from Roydent Dental Products of Johnson City, Tex.; ESPE™ EXPRESS™ impression material from 3M of St. Paul, Minn. In other embodiments, other materials are used to capture the bite record.

In other embodiments, the motion capture station 106 generates motion data 112 representing the movement of the arches relative to one another. In some embodiments, the motion capture station 106 generates the motion data 112 from optical measurements of the dental arches that are captured while the dentition of the patient is moved. In some embodiments, the optical measurements are extracted from image or video data recorded while the dentition of the patient is moved. Additionally, in some embodiments, the optical measurements are captured indirectly. For example, in some embodiments, the optical measurements are extracted from images or video data of one or more devices that are secured to a portion of the dentition of the patient. In some embodiments, the secured devices include intraoral extensions and/or extraoral extensions. Non-limiting examples of fiducial devices that can be secured to a portion of the dentition of the patient are illustrated and described with respect to at least FIGS. 34-35. In other embodiments, the motion data 112 is generated using other processes. Further, in some embodiments, the motion data 112 includes transformation matrices that represent the position and orientation of the dental arches. Other embodiments of the motion data 112 are possible as well.

In some embodiments, still images are captured of the patient's dentition while the dentition of the patient is positioned in a plurality of bite locations. In some embodiments, image processing techniques are used to determine the positions of the patient's upper and lower arches relative to each other (either directly or based on the positions of attached devices). In some embodiments, the motion data 112 is generated by interpolating between the positions of the upper and lower arches determined from at least some of the captured images.

The example dental lab 114 includes a 3D scanner 116, design system 118, rapid fabrication machine 126, and a restoration fabrication station 132. Although shown as a single dental lab in this figure, in some embodiments, the dental lab 114 comprises multiple dental labs. For example, in some embodiments, the 3D scanner 116 is in a different dental lab than one or more of the other components shown in the dental lab 114. Further, in some embodiments, one or more of the components shown in the dental lab 114 are not in a dental lab. For example, in some embodiments, one or more of the 3D scanner 116, design system 118, rapid fabrication machine 126, and restoration fabrication station 132 are in the dental office 102. Additionally, some embodiments of the system 100 do not include all of the components shown in the dental lab 114.

The example 3D scanner 116 is a device configured to create a three-dimensional digital representation of one or both of the dental impression 108 and the functional bite map 110. In some embodiments, the 3D scanner 116 generates a point cloud, a polygonal mesh, a parametric model, or voxel data representing the dental impression 108 or the functional bite map 110. In some embodiments, the 3D scanner 116 generates the digital dental model 120 or the functional bite map data 121. In some embodiments, the 3D scanner 116 comprises a laser scanner, a touch probe, or an industrial CT scanner. Yet other embodiments of the 3D scanner 116 are possible as well. Further, some embodiments of the system 100 do not include the 3D scanner 116. For example, in some embodiments of the system 100 where the dental impression station 104 generates a digital dental impression and the motion capture station 106 generates motion data 112, the 3D scanner 116 is not included.

The design system 118 is a system that is configured to generate one or both of the interference model data 122 and the dental restoration data 124. In some embodiments, the interference model data 122 is three-dimensional digital data that represents the interference model 128 and is in a format suitable for fabrication using the rapid fabrication machine 126. Similarly, in some embodiments, the dental restoration data 124 is three-dimensional digital data that represents the dental restoration component 130 and is in a format suitable for fabrication using the rapid fabrication machine 126.

In some embodiments, the design system 118 comprises a computing device including user input devices. In some embodiments, the design system 118 includes computer-aided-design (CAD) software that generates a graphical display of one or both of the interference model data 122 and the dental restoration data 124 and allows an operator to interact with and manipulate one or both of the interference model data 122 and the dental restoration data 124. In some embodiments, the design system 118 comprises digital tools that mimic the tools used by a laboratory technician to physically design a dental restoration. For example, some embodiments, include a tool to move the patient's dentition according to the motion data 112 (which may be similar to a physical articulator). Additionally, in some embodiments, the design system 118 comprises a server that partially or fully automates the generation of designs of one or both of the interference model data 122 and the dental restoration data 124.

In some embodiments, the rapid fabrication machine 126 comprises one or more three-dimensional printers, such as the ProJet line of printers from 3D Systems, Inc. of Rock Hill, S.C. Another example of the rapid fabrication machine 126 is stereolithography equipment. Yet another example of the rapid fabrication machine 126 is a milling device, such as a computer numerically controlled (CNC) milling device. In some embodiments, the rapid fabrication machine 126 is configured to receive files in the STL format. Other embodiments of the rapid fabrication machine 126 are possible as well.

In some embodiments, the rapid fabrication machine 126 is configured to use the interference model data 122 to fabricate the interference model 128. In some embodiments, the interference model 128 is a physical structure comprising a surface configured to oppose a dental restoration 134. In some embodiments, the interference model 128 is formed as a composite of the location of the dental arch opposite the dental restoration 134 along the various bite paths recorded by the functional bite map 110 or the motion data 112. In some embodiments, the interference model 128 comprises one or more retention structures that are configured to couple to a dental model and properly position the interference model 128 relative to the dental restoration 134. However, in some other embodiments, the restoration fabrication station 132 does not fabricate the interference model 128. For example, in some embodiments, a digital interference model is used by the design system 118 and it is not fabricated into a physical apparatus.

Additionally, in some embodiments, the rapid fabrication machine 126 is configured to use the dental restoration data 124 to fabricate the dental restoration component 130. In some embodiments, the dental restoration component 130 is a physical component that is configured to be used as part or all of the dental restoration 134. For example, in some embodiments, the dental restoration component is milled from zirconium or another material that is used directly as a dental restoration. In other embodiments, the dental restoration component 130 is a mold formed from wax or another material and is configured to be used indirectly (e.g., through a lost wax casting or ceramic pressing process) to fabricate the dental restoration 134. For example, in some embodiments, the dental restoration 134 is formed using traditional techniques (e.g., stacked porcelain or wax-up) using a dental model that includes the interference model 128.

In some embodiments, the restoration fabrication station 132 operates to fabricate a dental restoration 134 for the patient P. In some embodiments, the restoration fabrication station 132 uses the interference model 128 or the dental restoration component 130 produced by the rapid fabrication machine 126. In some embodiments, the dental restoration 134 is a filling, partial crown, full crown, veneer, bridge, complete denture, partial denture, or implant framework. Other embodiments of the dental restoration 134 are possible as well. In some embodiments, the dental restoration 134 is formed a from an acrylic, ceramic, or metallic material. In some embodiments, the dental impression 108 is used in the fabrication of the dental restoration 134. In some embodiments, the dental impression 108 is used to form a plaster model of the dentition of the patient P. Additionally, in some embodiments, a model of the dentition of the patient P is generated by the rapid fabrication machine 126. In some embodiments, the restoration fabrication station 132 comprises equipment and process to perform some or all of the techniques used in traditional dental laboratories to generate dental restorations. Other embodiments of the restoration fabrication station 132 are possible as well.

In some embodiments, the dental restoration 134 is seated in the mouth of the patient P in the restoration installation station 136 by a dentist D. In some embodiments, the dentist D confirms that the occlusal surface of the dental restoration 134 is properly defined by instructing the patient P to engage in various bites.

Additionally, in some embodiments, the dental office 102 is connected to the dental lab 114 by network 138.

The network 138 is an electronic communication network that facilitates communication between the dental office 102 and the dental lab 114. An electronic communication network is a set of computing devices and links between the computing devices. The computing devices in the network use the links to enable communication among the computing devices in the network. The network 138 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices.

In various embodiments, the network 138 includes various types of links. For example, the network 138 can include one or both of wired and wireless links, including Bluetooth, ultra-wideband (UWB), 802.11, ZigBee, and other types of wireless links. Furthermore, in various embodiments, the network 138 is implemented at various scales. For example, the network 138 can be implemented as one or more local area networks (LANs), metropolitan area networks, subnets, wide area networks (such as the Internet), or can be implemented at another scale.

Figure 2:
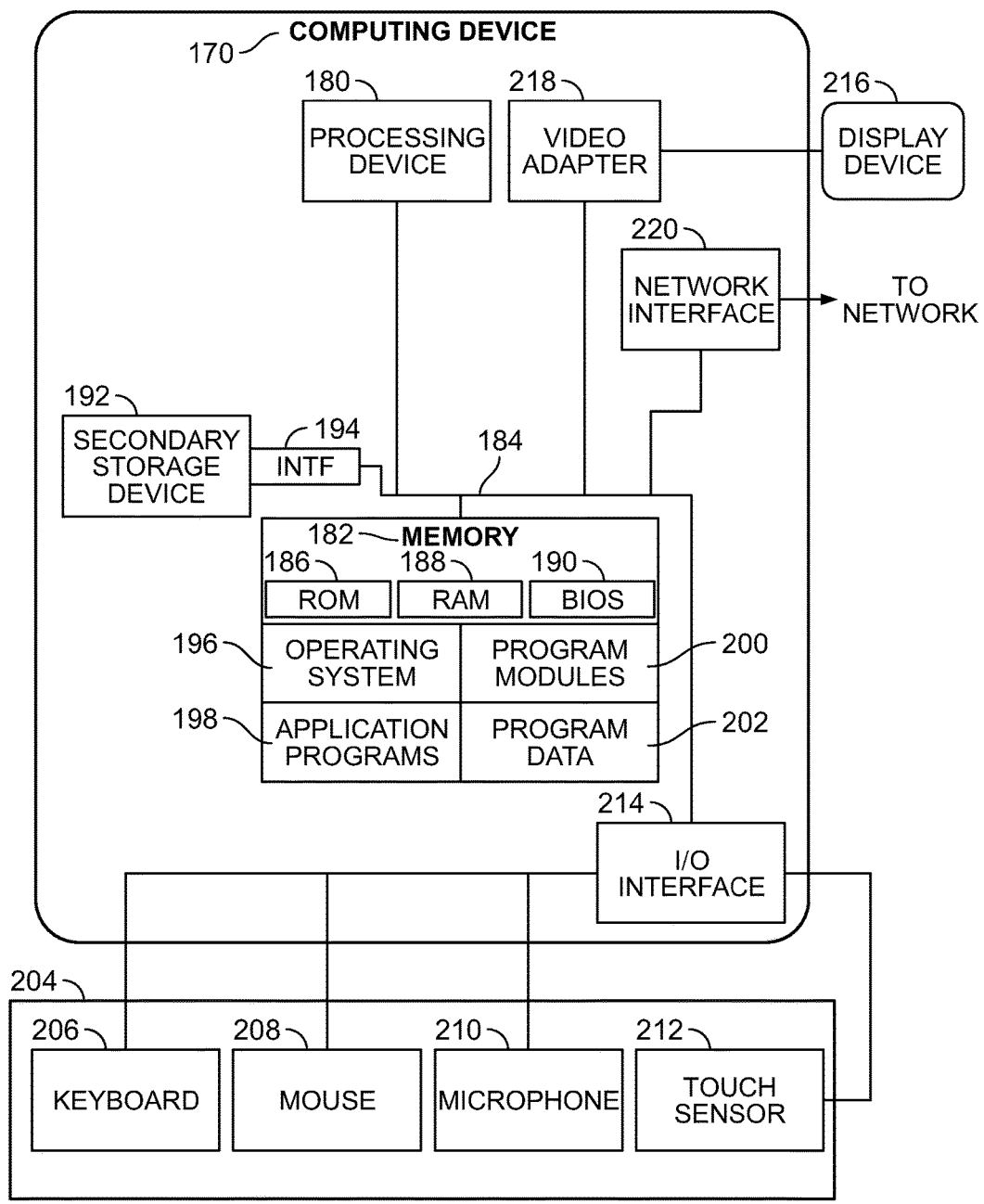
FIG. 2 illustrates an example architecture of a computing device, which can be used to implement aspects according to the present disclosure.

FIG. 2 illustrates an exemplary architecture of a computing device 160 that can be used to implement aspects of the present disclosure, including any of the plurality of computing devices described herein, such as a computing device of the dental impression station 104, motion capture station 106, 3D scanner 116, design system 118, rapid fabrication machine 126, restoration fabrication station 132, or any other computing devices that may be utilized in the various possible embodiments.

The computing device illustrated in FIG. 2 can be used to execute the operating system, application programs, and software modules (including the software engines) described herein.

The computing device 170 includes, in some embodiments, at least one processing device 180, such as a central processing unit (CPU). A variety of processing devices are available from a variety of manufacturers, for example, Intel or Advanced Micro Devices. In this example, the computing device 170 also includes a system memory 182, and a system bus 184 that couples various system components including the system memory 182 to the processing device 180. The system bus 184 is one of any number of types of bus structures including a memory bus, or memory controller; a peripheral bus; and a local bus using any of a variety of bus architectures.

Examples of computing devices suitable for the computing device 170 include a desktop computer, a laptop computer, a tablet computer, a mobile computing device (such as a smart phone, an iPod® or iPad® mobile digital device, or other mobile devices), or other devices configured to process digital instructions.

The system memory 182 includes read only memory 186 and random access memory 188. A basic input/output system 190 containing the basic routines that act to transfer information within computing device 170, such as during start up, is typically stored in the read only memory 186.

The computing device 170 also includes a secondary storage device 192 in some embodiments, such as a hard disk drive, for storing digital data. The secondary storage device 192 is connected to the system bus 184 by a secondary storage interface 194. The secondary storage devices 192 and their associated computer readable media provide nonvolatile storage of computer readable instructions (including application programs and program modules), data structures, and other data for the computing device 170.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media. Additionally, such computer readable storage media can include local storage or cloud-based storage.

A number of program modules can be stored in secondary storage device 192 or system memory 182, including an operating system 196, one or more application programs 198, other program modules 200 (such as the software engines described herein), and program data 202. The computing device 170 can utilize any suitable operating system, such as Microsoft Windows™, Google Chrome™ OS, Apple OS, Unix, or Linux and variants and any other operating system suitable for a computing device. Other examples can include Microsoft, Google, or Apple operating systems, or any other suitable operating system used in tablet computing devices.

In some embodiments, a user provides inputs to the computing device 170 through one or more input devices 204. Examples of input devices 204 include a keyboard 206, mouse 208, microphone 210, and touch sensor 212 (such as a touchpad or touch sensitive display). Other embodiments include other input devices 204. The input devices are often connected to the processing device 180 through an input/output interface 214 that is coupled to the system bus 184. These input devices 204 can be connected by any number of input/output interfaces, such as a parallel port, serial port, game port, or a universal serial bus. Wireless communication between input devices and the interface 214 is possible as well, and includes infrared, BLUETOOTH® wireless technology, 802.11a/b/g/n, cellular, ultra-wideband (UWB), ZigBee, or other radio frequency communication systems in some possible embodiments.

In this example embodiment, a display device 216, such as a monitor, liquid crystal display device, projector, or touch sensitive display device, is also connected to the system bus 184 via an interface, such as a video adapter 218. In addition to the display device 216, the computing device 170 can include various other peripheral devices (not shown), such as speakers or a printer.

When used in a local area networking environment or a wide area networking environment (such as the Internet), the computing device 170 is typically connected to the network through a network interface 220, such as an Ethernet interface. Other possible embodiments use other communication devices. For example, some embodiments of the computing device 170 include a modem for communicating across the network.

The computing device 170 typically includes at least some form of computer readable media. Computer readable media includes any available media that can be accessed by the computing device 170. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 170.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 2 is also an example of programmable electronics, which may include one or more such computing devices, and when multiple computing devices are included, such computing devices can be coupled together with a suitable data communication network so as to collectively perform the various functions, methods, or operations disclosed herein.

Figure 3:
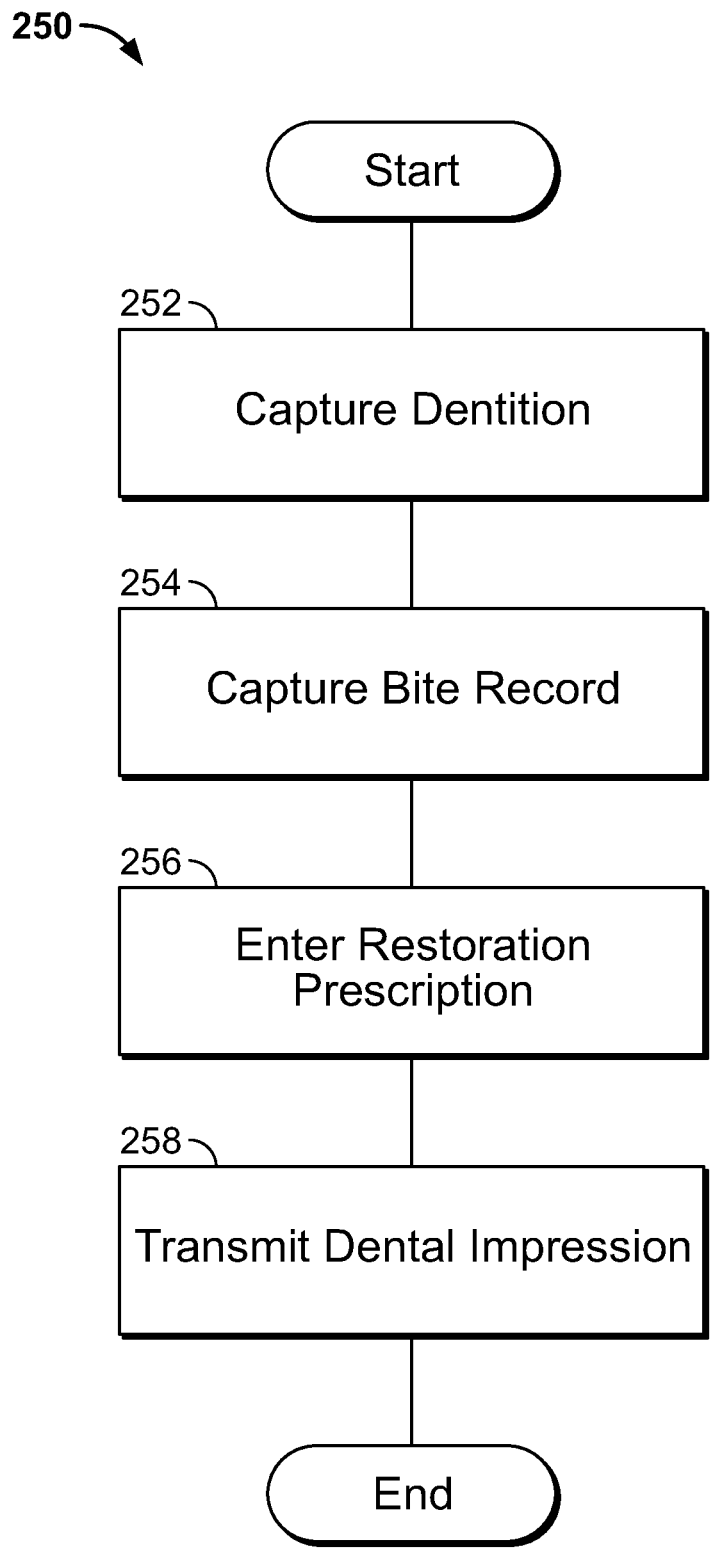
FIG. 3 is a flow chart illustrating an example method of capturing a dental impression using embodiments of the system of FIG. 1.

FIG. 3 is a flow chart illustrating an example method 250 of capturing a dental impression. In some embodiments, the method 250 is performed at the dental impression station 104. In this example, the method 250 includes operations 252, 254, 256, and 258.

At operation 252, the dentition of the patient P is captured. As described above with respect to FIG. 1, in some embodiments, the dentition is captured using a physical impression material and in other embodiments, the dentition is captured using a digital impression system.

At operation 254, the bite record of the patient P is captured. In some embodiments, the bite record comprises information about contact between the upper dentition and lower dentition of the patient. In some embodiments, the bite record is captured in one or more of following positions: centric occlusion, centric relation, and various excursive bite positions. In some embodiments, this operation is not performed and the bite record is not captured.

In some embodiments, the bite record is captured using a bite registration material such as bite registration wax or polysiloxane. A bite registration material captures the relationship between the upper and lower dentition of the patient P as indents when the patient P bites into the material.

At operation 256, the restoration prescription is entered. In some embodiments, the restoration prescription comprises information about the type of restoration the doctor D is prescribing for the patient P. In some embodiments, the restoration prescription includes the identity of the tooth or teeth that are being restored, the desired restoration material/s, the desired type of restoration, and additional instructions for fabricating the restoration. In some embodiments, the restoration prescription is entered into a computing device where it is stored. In other embodiments, the restoration prescription is entered into a paper form. Other embodiments are possible as well.

At operation 258, the dental impression 108 is transmitted. In some embodiments, the dental impression 108 is transmitted to the dental lab 114. In some embodiments, the bite record captured in operation 254 and the restoration prescription entered in operation 256 are transmitted with the dental impression 108. In some embodiments, the dental impression 108 is transmitted across the network 138 as a digital impression. In other embodiments, the dental impression 108 is transmitted as a physical dental impression or dental model.

Figure 4:
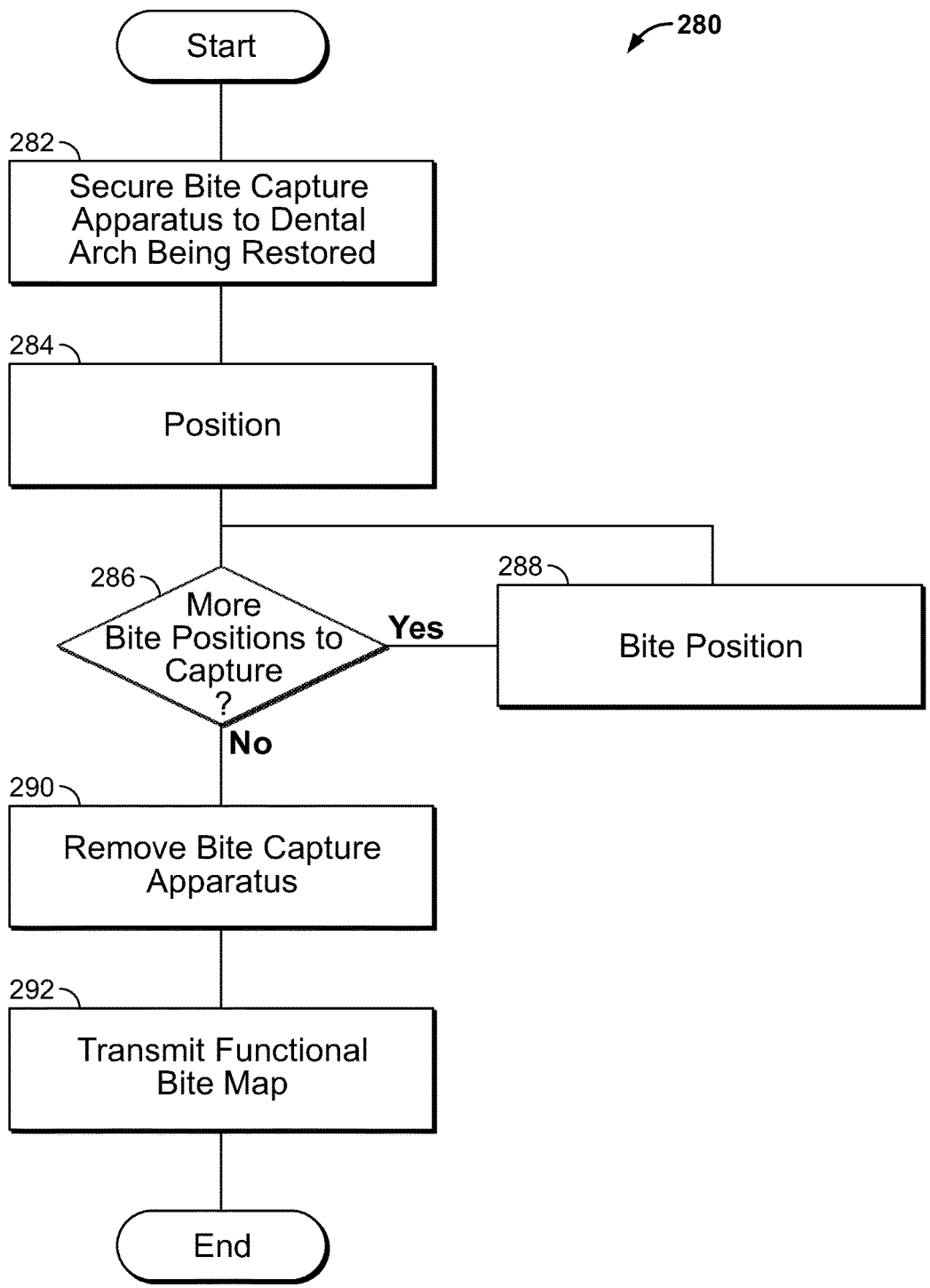
FIG. 4 is an example process performed at some embodiments of the motion capture station 106 of FIG. 1.

FIG. 4 is an example process 280 performed at some embodiments of the motion capture station 106.

At operation 282, the bite capture apparatus is secured to the dental arch that includes the tooth or teeth that are being restored. In some embodiments, the bite capture apparatus is secured so that it is substantially immovable relative the dental arch that includes the tooth or teeth that are being restored. In some embodiments, the bite capture apparatus includes a first surface that is configured to secure the bite capture apparatus to a dental arch, and a second surface that is configured to record the relative movement of the opposite arch.

At operation 284, the patient's jaw is closed into a first bite position. For example, in some embodiments, the patient's jaw is closed into a centric bite. In some embodiments, the patient is instructed to bite into the bite capture apparatus. In other embodiments, the dentist or another caregiver may physically guide the patient's jaw into the bite position.

At operation 286, it is determined whether there are more bite positions to capture. For example, in some embodiments, the patient's bite will be captured in some or all of the following positions: centric, excursive, left lateral, and right lateral. If there are more bite positions to capture, the process 280 continues to operation 288, where the patient's bite is moved into the next bite position. In some embodiments, the patient continues to apply bite force on the bite capture apparatus as the bite is moved to the next bite position. In this manner, the bite capture apparatus record the relative location of the opposing dentition throughout the full bite path. If there are not any more bite positions to capture, the process 280 continues to operation 290.

At operation 290, the bite capture apparatus is removed from the dentition of the patient. In some embodiments, at this point, the bite capture apparatus will have recorded the relative location of the opposing dentition in all bite positions and all bite paths between those bite positions.

At operation 292, the functional bite map 110 is transmitted. In some embodiments, the functional bite map 110 is transmitted to the dental lab 114. In some embodiments, the functional bite map 110 comprises the entire bite capture apparatus. In other embodiments, the functional bite map comprises only the portion (e.g., the motion capture layer) of the bite capture apparatus that includes the indents corresponding to the relative locations of the patient P's dentition in various bite positions and along the paths between those positions. In some embodiments, the functional bite map 110 is transmitted across the network 138 after being digitized using a three-dimensional scanner, such as an impression scanner. In other embodiments, the functional bite map 110 is transmitted as a physical dental impression or dental model.

Figure 5:
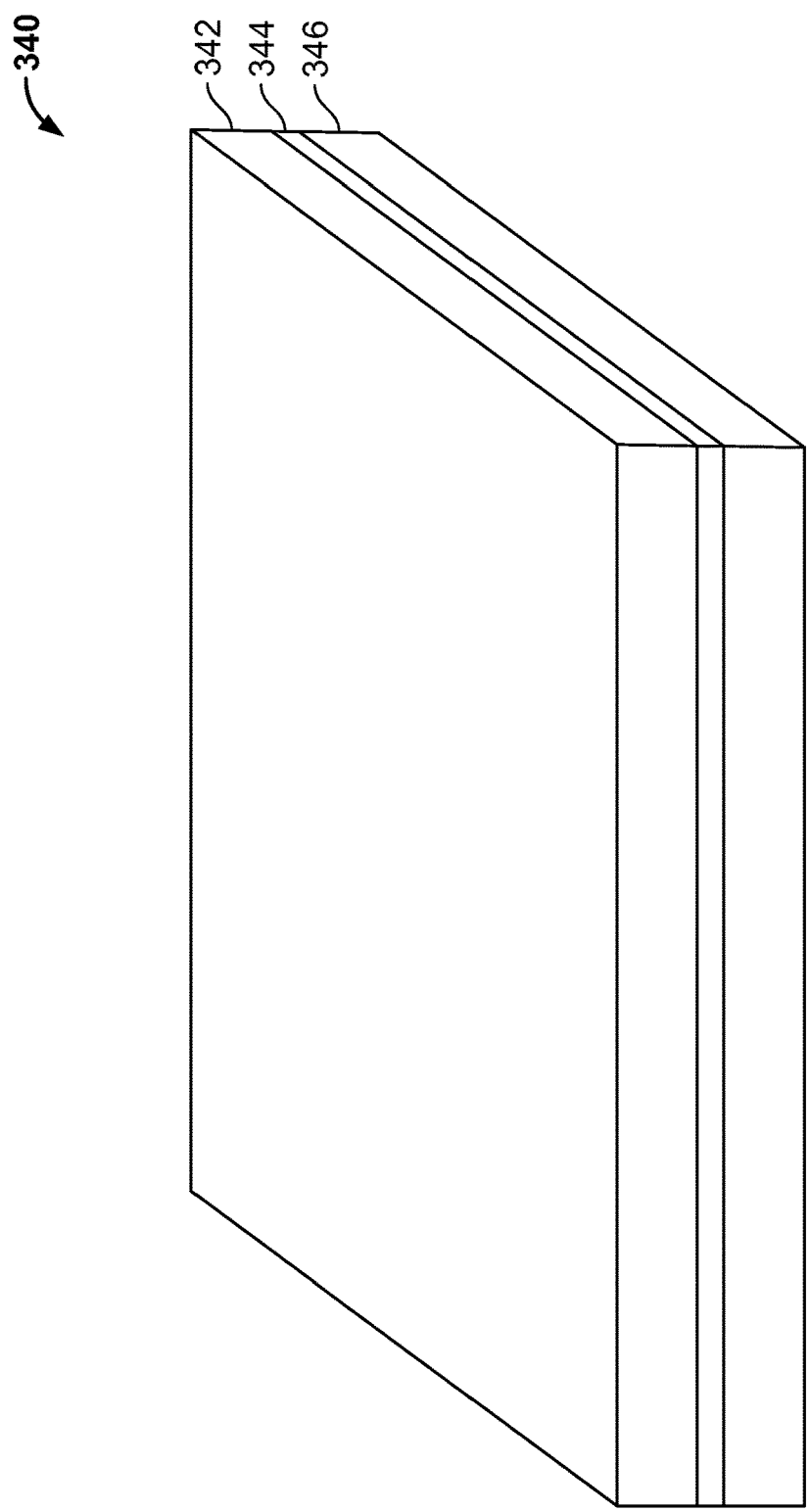
FIG. 5 is an example embodiment of a bite capture apparatus for capturing the functional bite map of FIG. 1.

FIG. 5 is an example embodiment of a bite capture apparatus 340 for capturing a functional bite map 110. In some embodiments, the bite capture apparatus 340 is used at the motion capture station 106. In some embodiments, the bite capture apparatus includes a securing layer 342, a separating layer 344, and a motion capture layer 346. In some embodiments, the bite capture apparatus 340 is configured to be placed in the patient's mouth and bitten into by the patient P.

The securing layer 342 is an apparatus and is configured to secure the bite capture apparatus 340 to the dentition of the patient. In some embodiments, the securing layer 342 comprises a layer of material. In other embodiments, the securing layer 342 comprises one or mechanical devices configured to secure the bite capture apparatus 340 to one or more of the teeth in patient's dentition. In some embodiments, the securing layer 342 is configured to be secured to the maxillary arch. In other embodiments, the bite capture layer is configured to be secured mandibular arch. In other embodiments, the securing layer 342 is configured to be secured to either arch.

In some embodiments, the securing layer 342 is formed from an impression material, such as vinyl polysiloxane, wax, or other materials. For example, in some embodiments, the securing layer 342 is formed from a thixotropic vinyl polysiloxane, such as BLU-MOUSSE® from Parkell Inc. in Edgewood, N.Y. In some embodiments, the securing layer 342 is warmed and the pressed into the dentition of the patient until it cools and hardens or becomes substantially rigid. In some embodiments, the securing layer 342 is very thin after it is secured to the patient's dentition. For example, in some embodiments, the securing layer 342 is less than fifty micrometers thick. In yet other embodiments, at least some points on the dentition create holes in the securing layer 342. In some embodiments, this advantageously minimizes the amount of interference to the patient's bite that is caused by the presence of the securing layer 342.

The separating layer 344 is configured to separate the securing layer 342 from the motion capture layer 346. In some embodiments, the separating layer 344 is formed from a thin sheet of foil or plastic. For example, in some embodiments, the separating layer 344 is between 5-50 micrometers thick.

The motion capture layer 346 is a layer of material configured to capture the relative motion of the patient's teeth. In some embodiments, the motion capture layer 346 captures indentations created by the patient's teeth on the arch opposing the teeth the bite capture apparatus 340 is secured to. In some embodiments, the motion capture layer 346 is formed from wax that remains pliable at room temperature. In other embodiments, the motion capture layer is formed from other materials.

Figure 6:
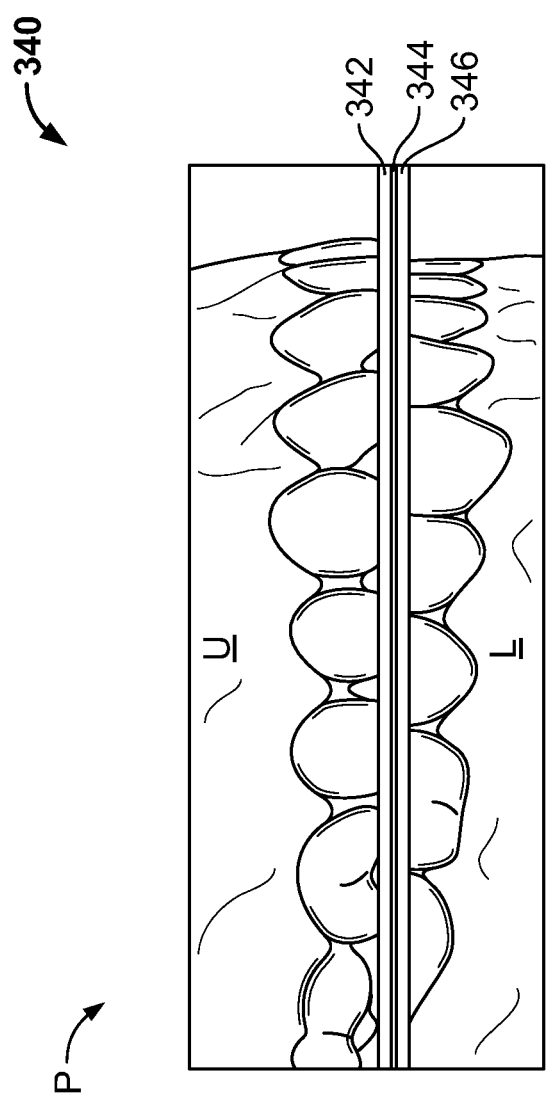
FIG. 6 is an illustration of an embodiment of the bite capture apparatus of FIG. 5 being used to capture bite motion information of a patient.

FIG. 6 is an illustration of an embodiment of the bite capture apparatus 340 being used to capture bite motion information of a patient P. The upper arch U and the lower arch of the patient P are shown.

In this example, the securing layer 342 is secured to the upper arch U and the motion capture layer 346 is configured to capture indentations made by the lower arch L. In this manner, if the patient P moves between different bite positions, the motion capture layer 346 will include indentations that represent the location of the lower arch L relative to the upper arch U in the various bite positions and on the bite paths between those positions.

Figure 7:
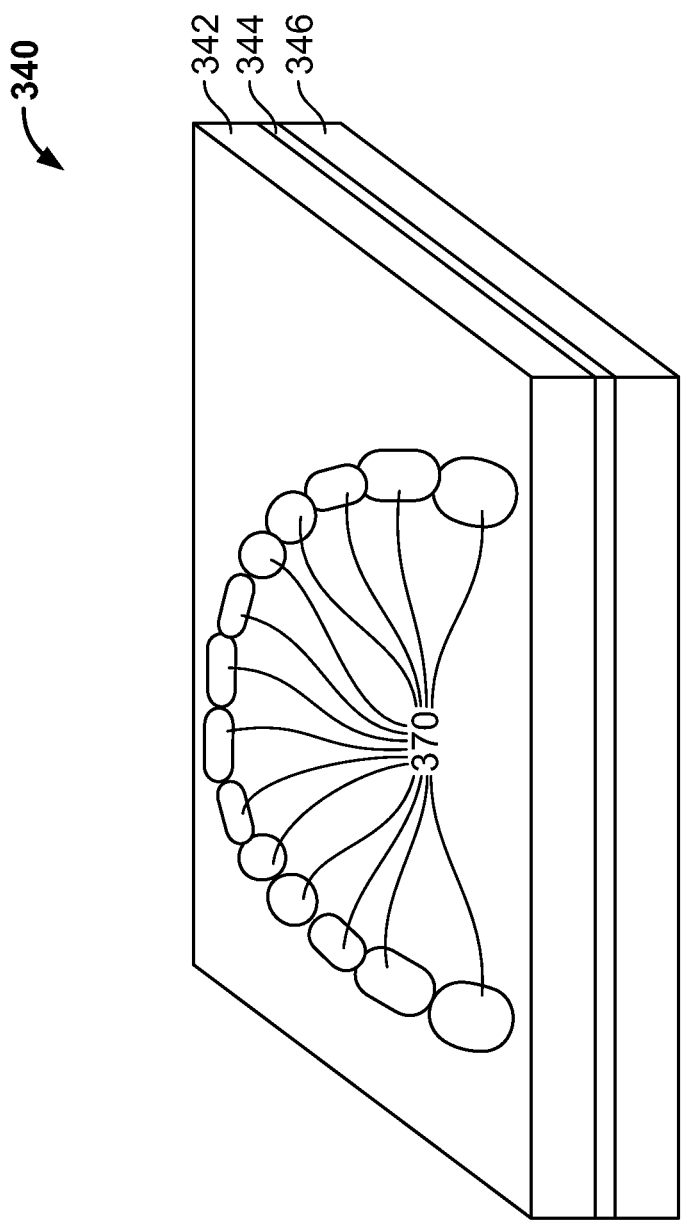
FIG. 7 is an illustration of an embodiment of the bite capture apparatus of FIG. 5 after the securing layer has formed to the patient's dentition.

FIG. 7 is an illustration of an embodiment of the bite capture apparatus 340 after the securing layer 342 has formed to the patient P's dentition. In this example, the securing layer 342 includes securing indents 370. In some embodiments, the securing indents 370 correspond to the positions and shapes of the teeth the bite capture apparatus 340 is configured to be secured to. In some embodiments, the securing indents 370 are formed when the securing layer 342 is pressed against the teeth of the patient P. In some embodiments, the securing layer 342 is soft and pliable at the time it is pressed against the patient P's teeth. Further, in some embodiments, the securing layer 342 cures or hardens after a time period.

Figure 8:
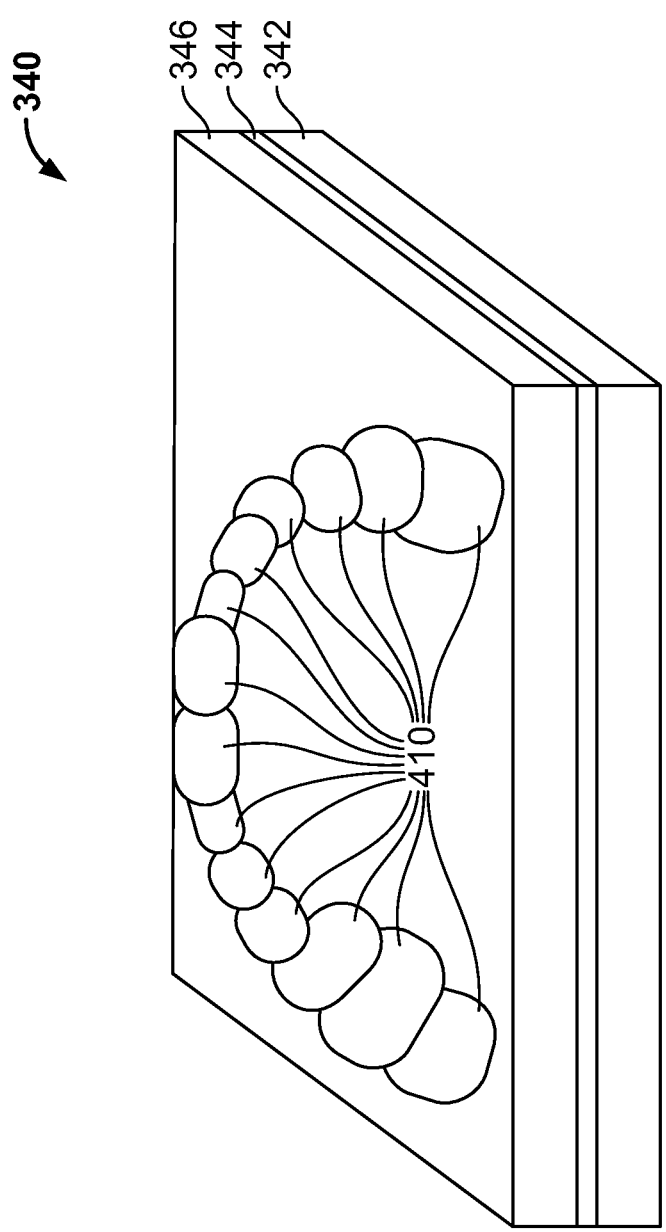
FIG. 8 is an illustration of an embodiment of the bite capture apparatus of FIG. 5 after the motion capture layer has captured the relative motion from the patient's dentition.

FIG. 8 is an illustration of an embodiment of the bite capture apparatus 340 after the motion capture layer 346 has captured the relative motion from the patient P's dentition. In this example, the motion capture layer 346 includes motion indents 410. In some embodiments, the motion indents 410 correspond to the relative positions of the teeth opposite of the securing layer 342. In some embodiments, the motion indents 410 are formed when the patient P's jaw is positioned and moved between various bite positions. In some embodiments, the motion indents 410 represent a union of the teeth in multiple bite positions. In some embodiments, the motion capture layer 346 remains soft and pliable throughout the time the patient is wearing the bite capture apparatus 340.

Figure 9:
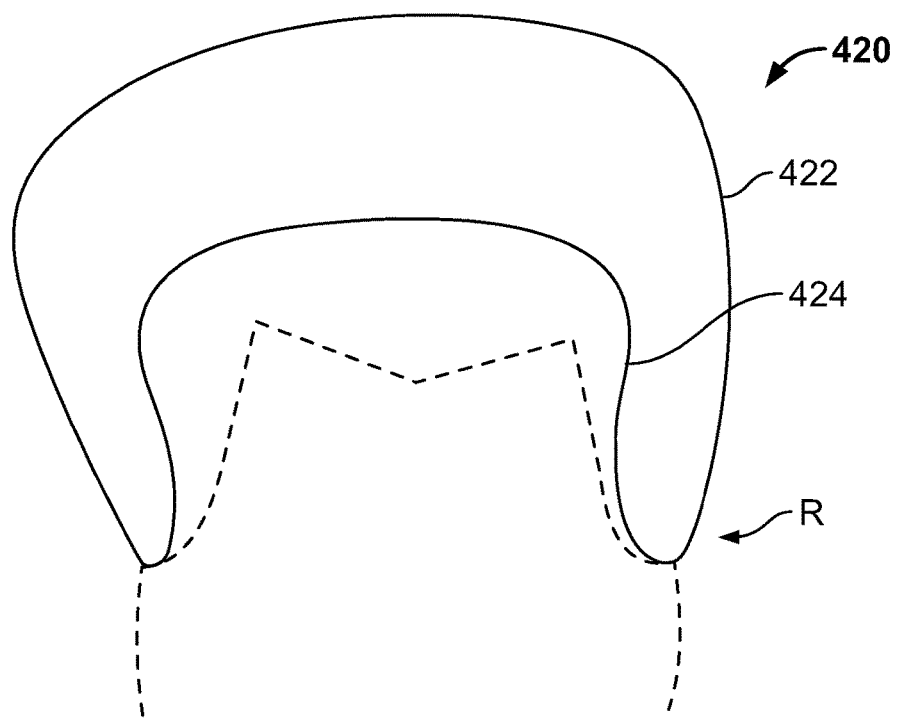
FIG. 9 is another example embodiment of a bite capture apparatus for capturing the functional bite map of FIG. 1.

FIG. 9 is another example embodiment of a bite capture apparatus 420 for capturing a functional bite map 110. In some embodiments, the bite capture apparatus 420 is used at the motion capture station 106. In some embodiments, the bite capture apparatus 420 includes a motion capture structure 422 and a securing structure 424. The bite capture apparatus 420 is configured to be secured to a restoration site R of the patient.

The motion capture structure 422 is a structure configured to capture the relative motion of the patient's teeth. In some embodiments, the motion capture structure 422 captures indentations created by the patient's teeth on the arch opposing the restoration site the bite capture apparatus 420 is secured to. In some embodiments, the motion capture layer 346 is formed from a pliable wax. In other embodiments, the motion capture layer 346 is formed from a combination of wax and a metal, such as copper or aluminum. In other embodiments, the motion capture layer is formed from other materials.

In some embodiments, the motion capture structure 422 has a bulbous or spherical shape. In some embodiments, the motion capture structure 422 has a shape that is similar to a large, bulbous tooth. In other embodiments, the motion capture structure 422 has another shape.

The securing structure 424 is a structure that operates to secure the bite capture apparatus 420 to the restoration site R. In some embodiments, the securing structure 424 is a cavity that is large enough to fit over the restoration site R. In some embodiments, the securing structure 424 is configured to be secured to the restoration site R by filling the securing structure 424 with a quick-set vinyl polysiloxane material and then placing the bite capture apparatus 420 over the restoration site R.

In some embodiments, the motion capture structure 422 is similar to a pre-fabricated crown, such as an anodized crown, except that it is more bulbous and lacks dental anatomy.

Figure 10:
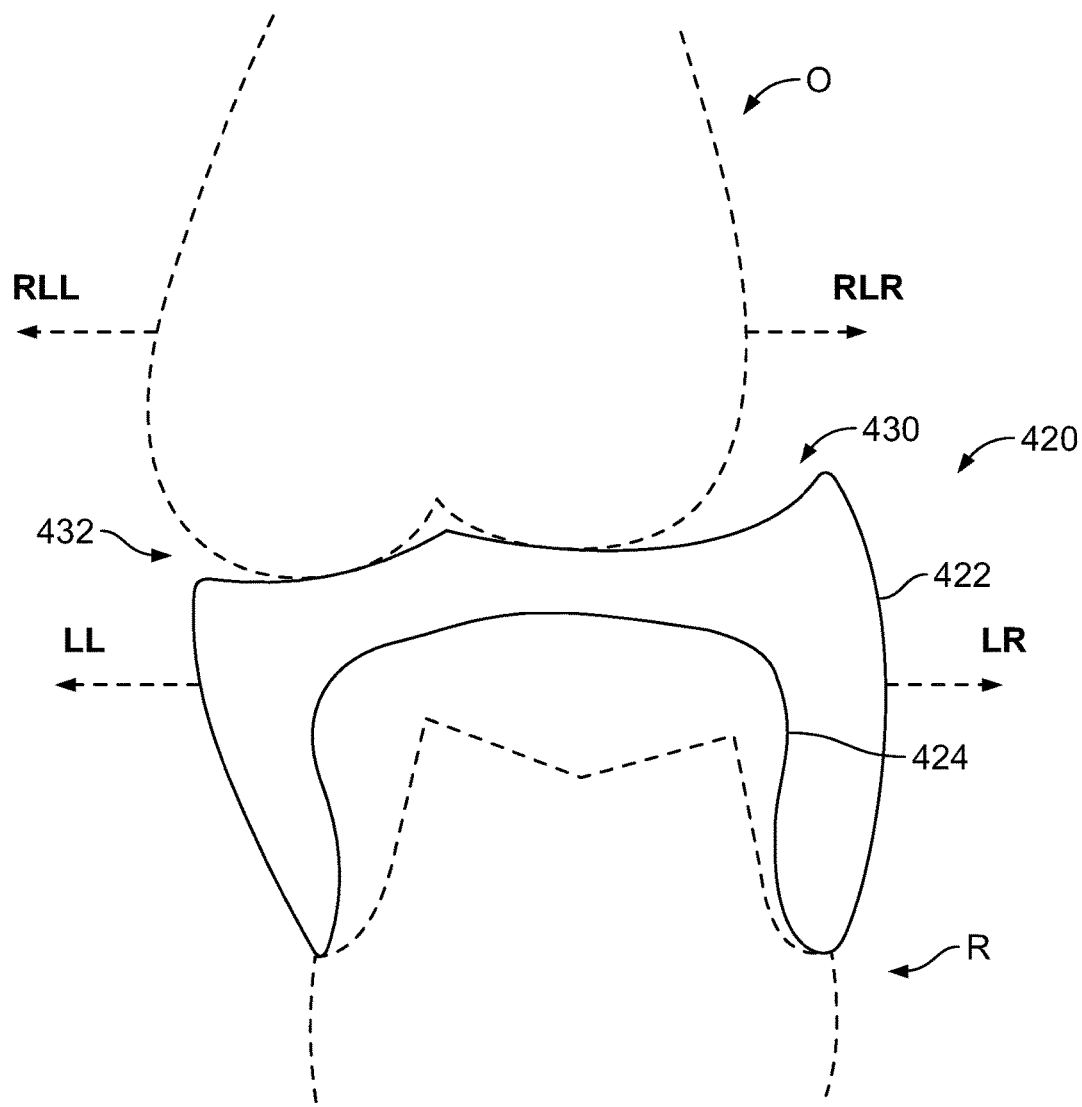
FIG. 10 is an illustration of the bite capture apparatus of FIG. 9 after the motion capture structure has captured the relative motion from the opposing dentition of the patient.

FIG. 10 is an illustration of the bite capture apparatus 420 after the motion capture structure 422 has captured the relative motion from the opposing dentition O of the patient P. The motion capture structure 422 now includes indents 430 and 432 that were created by the opposing dentition O as it moved, relative to the restoration site R, through various bite paths. Although the lower arch moves relative to the rest of the patient P's head, for purposes of the bite capture apparatus 420 it is the motion relative to the restoration site R that is captured. In FIG. 10, the motion arrows LL and LR are shown as well as the relative motion arrows RLL and RLR.

The arrow RLL indicates the direction in which the opposing dentition O moves relative to the restoration site R in a lateral left direction (e.g., as would occur when the lower arch moves along a lateral right bite path indicated by the motion arrow LR). When the restoration site R moves in the direction LR, the opposing dentition O moves in the direction of the arrow RLL relative to the restoration site R and the opposing dentition O carves out part of the indent 432.

The arrow RLR indicates the direction in which the opposing dentition O moves relative to the restoration site R in a lateral right direction (e.g., as would occur when the lower arch moves along a lateral left bite path indicated by the motion arrow LL). When the restoration site R moves in the direction LL, the opposing dentition O moves in the direction of the arrow RLR and the opposing dentition O carves out part of the indent 430.

In some embodiments, after the motion capture structure 422 has captured indents representing some or all of the bite paths and positions of the patient P, the bite capture apparatus 420 is removed from the restoration site R so that it can be transmitted to the dental lab 114. In some embodiments, the bite capture apparatus 420 is transmitted to the dental lab 114 by being physically delivered. Once transmitted to the dental lab 114, in some embodiments, the bite capture apparatus 420 is placed on a plaster model of restoration site R and scanned by the 3D scanner 116.

In other embodiments, after the motion capture structure 422 has captured indents representing some or all of the bite paths and positions of the patient P, the bite capture apparatus 420 is scanned using a digital impressioning system and then transmitted digitally to the dental lab 114. Other embodiments are possible as well.

Figure 11:
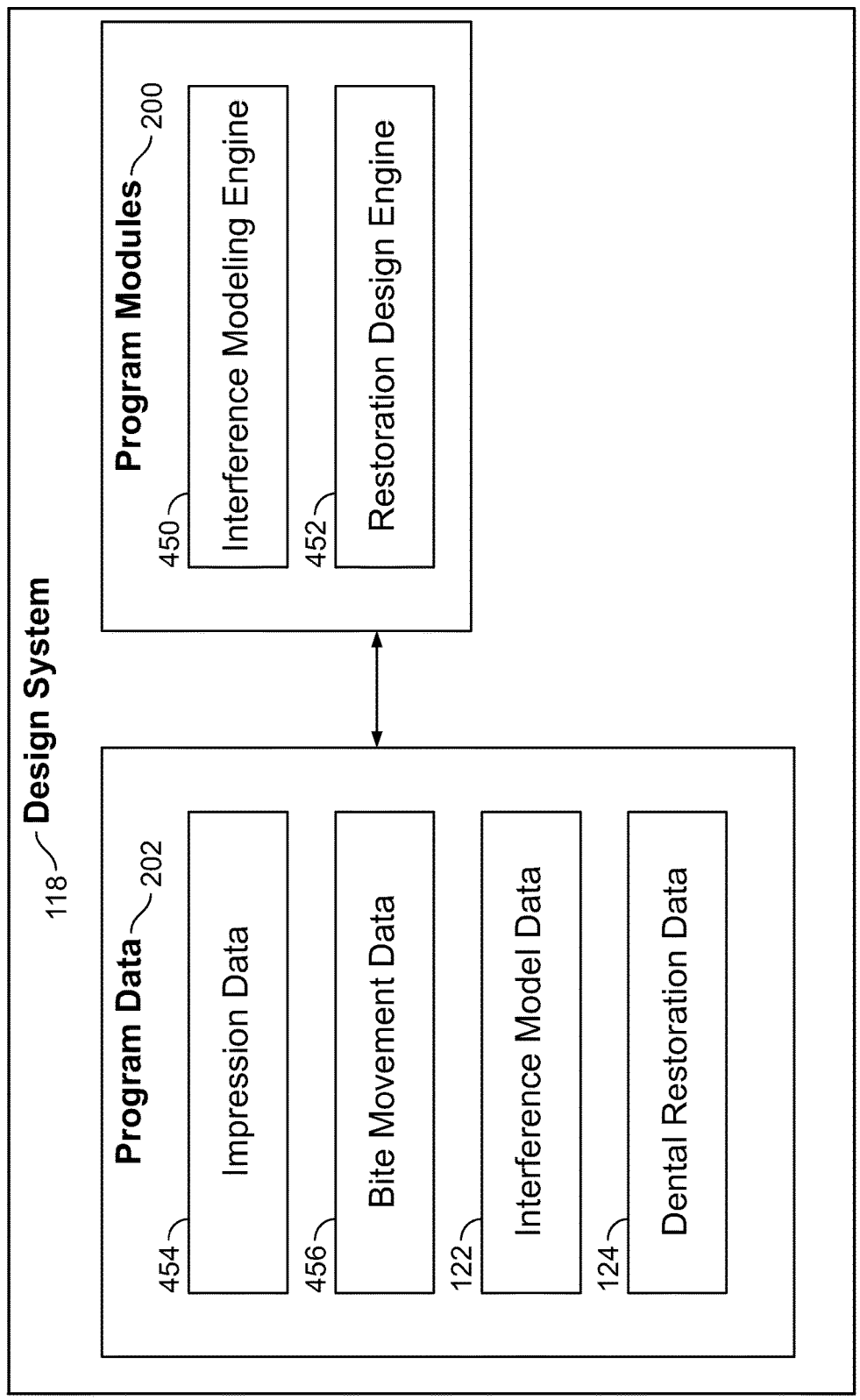
FIG. 11 illustrates an exemplary architecture of the program modules and program data of the design system of FIG. 1.

FIG. 11 illustrates an exemplary architecture of the program modules 200 and program data 202 of the design system 118. The program modules 200 include a plurality of modules that, when executed by the processing device 180 (shown in FIG. 2), perform one or more operations of the design system 118. The modules include an interference modeling engine 450 and a restoration design engine 452. In some embodiments, the program modules 200 includes more, fewer, or different modules than those shown in FIG. 11.

The program data 202 is stored in a data storage device, such as the memory 182 or the secondary storage device 192 (shown in FIG. 2). In some embodiments, program data 202 includes impression data 454, bite movement data 456, the interference model data 122, and the dental restoration data 124. In some embodiments, the program data 202 include more, fewer, or different types of data than the data shown in FIG. 9.

In some embodiments, the data stored in program data 202 can be represented in one or more files having any format usable by a computer. Examples include text files formatted according to a markup language and having data items and tags to instruct computer programs and processes how to use and present the data item. Examples of such formats include html, xml, and xhtml, although other formats for text files can be used. Additionally, the data can be represented using formats other than those conforming to a markup language.

The interference modeling engine 450 operates to generate the interference model data 122. In some embodiments, the interference modeling engine 450 uses the impression data 454 and the bite movement data 456 to generate the interference model data 122.

The restoration design engine 452 operates to generate the dental restoration data 124. In some embodiments, the restoration design engine 452 uses the impression data 454 and the interference model data 122 to generate the dental restoration data 124.

Figure 12:
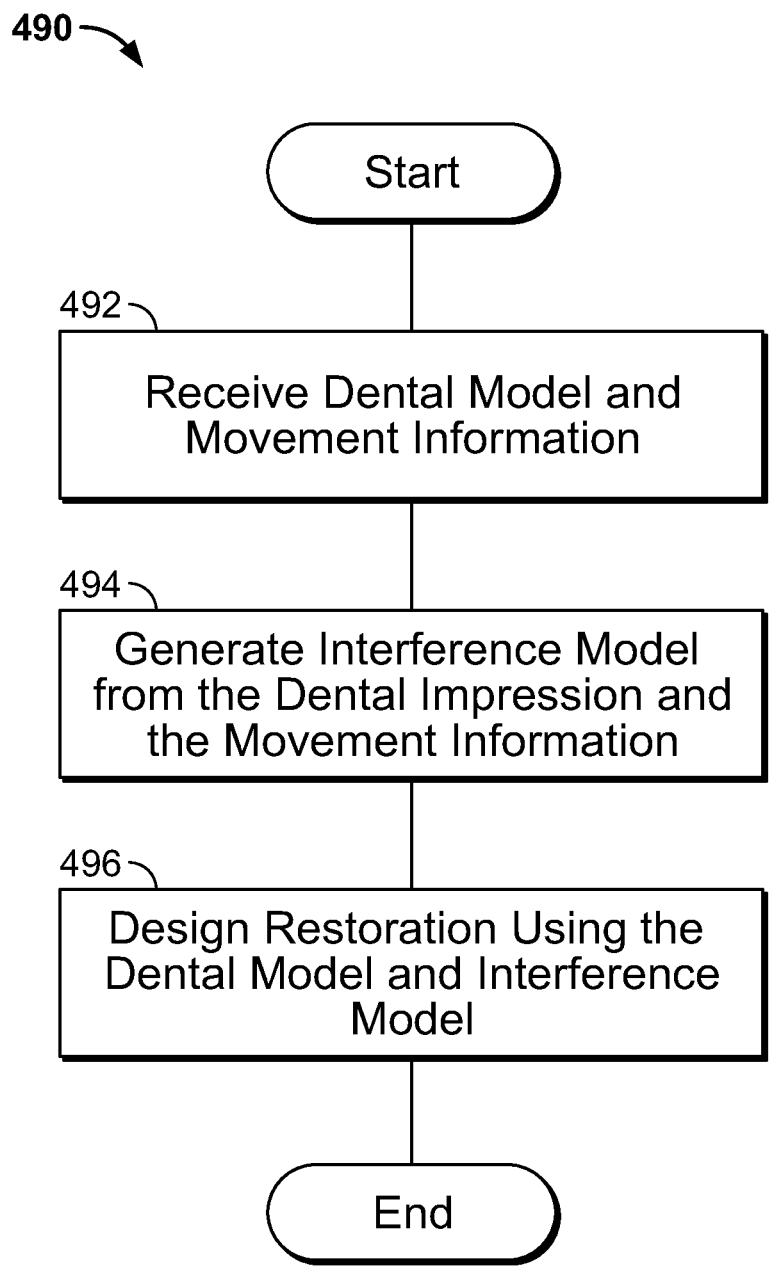
FIG. 12 is a flow chart illustrating an example method of fabricating the dental restoration using the interference model data of FIG. 1.

FIG. 12 is a flow chart illustrating an example method 490 of fabricating the dental restoration 134 using the interference model data 122. In some embodiments, the method 490 is performed by the interference modeling engine 450 and the restoration design engine 452 using a processor (such as processing device 180, shown in FIG. 2). In this example, the method 490 includes operations 492, 494, and 496.

At operation 492, the digital dental model 120 and movement information are received. In some embodiments, the digital dental model 120 is generated from a dental impression 108 that is transmitted digitally by the dental impression station 104 and is converted into the digital dental model 120.

In other embodiments, the digital model is generated from a physical impression. In some of these embodiments, the dental impression 108 is scanned by the 3D scanner 116 to create the digital dental model 120. In other of these embodiments, a plaster model is formed from the physical impression and then the plaster model is scanned by the 3D scanner 116 to create the digital dental model 120. Other embodiments are possible as well.

In some embodiments, the movement information is received as motion data 112 directly from the motion capture station 106. In other embodiments, the movement information is received as functional bite map data 121 that is generated by scanning the functional bite map 110 using the 3D scanner 116.

At operation 494, the interference model data 122 is generated from the dental impression and the movement information. In some embodiments, the interference model data 122 represents a polygonal surface. In other embodiments, the interference model data represents a polygonal model. In some embodiments, the interference model data 122 comprises a surface of the functional bite map data 121. In other embodiments, the interference model data 122 is generated by sweeping a portion of the digital dental model 120 along the movement path recorded in the motion data 112. In some embodiments, a portion of the dental arch that opposes the site for the dental restoration 134 is swept along the movement paths. In other embodiments, the interference model data 122 is generated by using Boolean operations to generate a model that the represents the union of the opposing dentition in multiple bite locations.

At operation 496, the restoration is designed using the digital dental model 120 and the interference model. In some embodiments, the interference model is visualized in relation to the restoration site. In some embodiments, an operator utilizes a user interface to design the dental restoration data 124 to avoid contact with the interference model. In other embodiments, the dental restoration data 124 is designed automatically by the restoration design engine to avoid contact with a digital interference model.

Figure 13:
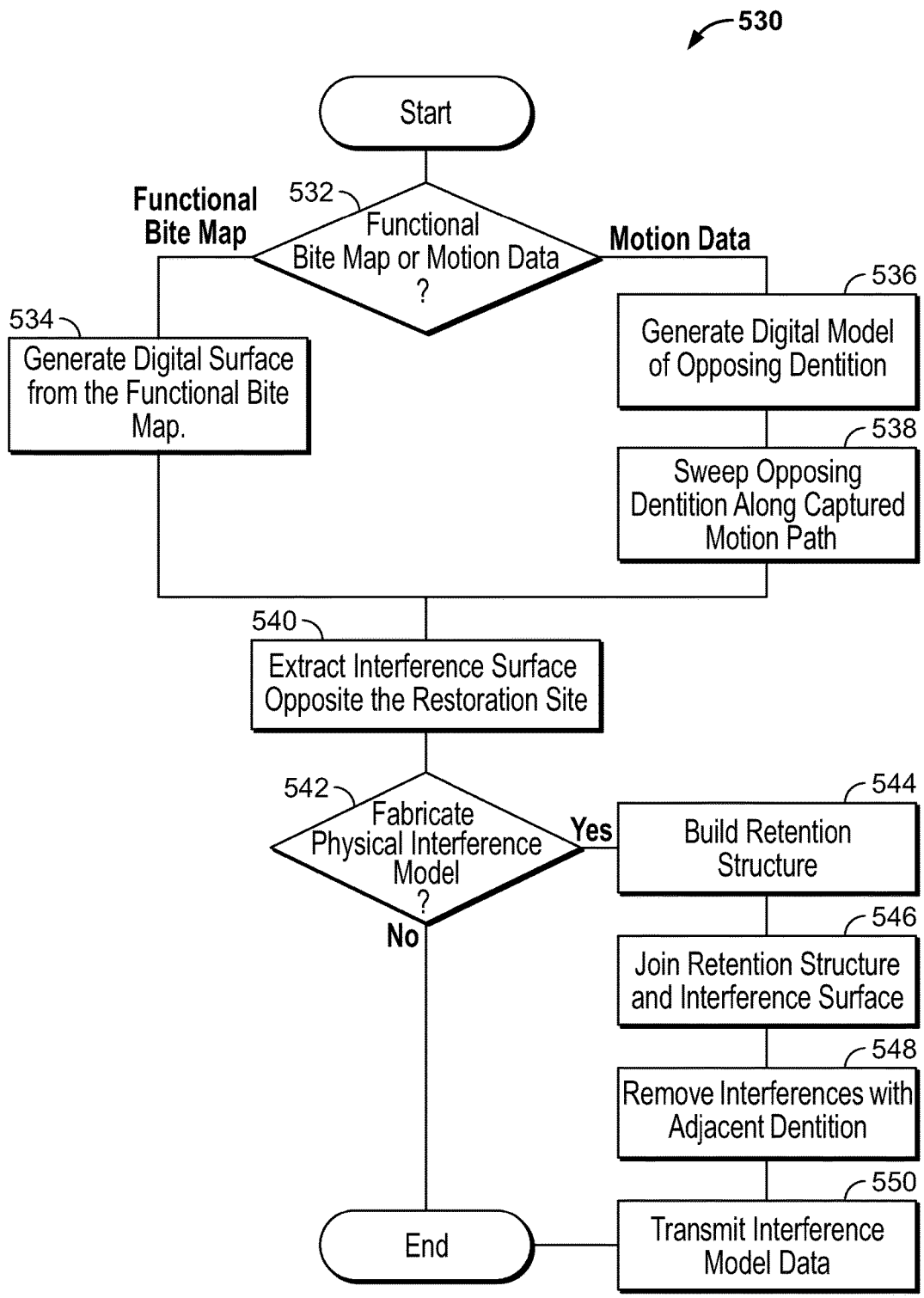
FIG. 13 is a flow chart illustrating an example method of fabricating the interference model using the interference model data of FIG. 1.

FIG. 13 is a flow chart illustrating an example method 530 of fabricating the interference model 128 using the interference model data 122. In some embodiments, the method 530 is performed by the restoration design engine 452 using a processor (such as processing device 180, shown in FIG. 2). In this example, the method 530 includes operations 532, 534, 536, 538, 540, 542, 544, 546, 548, and 550.

At operation 532 it is determined whether a functional bite map 110 or motion data 112 is provided. If a functional bite map 110 is provided, the method 530 continues to operation 534. If not, the method 530 continues to operation 536.

At operation 534, a digital surface is generated from the functional bite map 110.

At operation 536, a digital model of the opposing dentition is generated. At operation 538, the digital model of the opposing dentition is swept along the movement path/s recorded in the motion data 112.

At operation 540, an interference surface opposing the restoration site is extracted. In some embodiments, the interference surface is extracted from the digital surface generated from the functional bite map 110 at operation 534. In other embodiments, the interference surface is extracted from the sweep of the digital model of the opposing dentition at operation 538. In some embodiments, only a portion of the interference surface is extracted. For example, in some embodiments, a portion of the interference surface directly opposite the restoration site is extracted. In other embodiments, a larger portion of the occlusal surface is extracted. For example, in some embodiments, a portion of the interference surface opposing the teeth adjacent to the restoration site is extracted as well.

At operation 542, it is determined whether a physical interference model will be Fabricated. If so, the method 530 continues to operation 544. If not, the method 530 ends and the interference surface extracted at operation 540 is ready for use in digital dental design.

At operation 544, a retention structure is built. The retention structure operates to align the interference surface to a physical model of the patient P's dentition. In some embodiments, the retention structure is configured to secured the interference surface to the patient P's dentition. In other embodiments, the retention structure is configured to align the interference surface without securing it. In some embodiments, the retention structure is a band, clasp, or surface that matches the contour of the adjacent dentition. In other embodiments, the retention structure is a male or female connector that is configured to mate with an opposite connector that is added to the physical model of the patient P's dentition. Other embodiments are possible as well.

At operation 546, the retention structure is joined to the interference structure to form an integral digital interference model.

At operation 548, interferences with the adjacent dentition are removed from the interference surface. In some embodiments, this ensures that interferences with the adjacent teeth do not prevent the interference surface from being properly aligned relative to the restoration site.

At operation 550, the interference model data is transmitted to the rapid fabrication machine 126 for fabrication.

Figure 14:
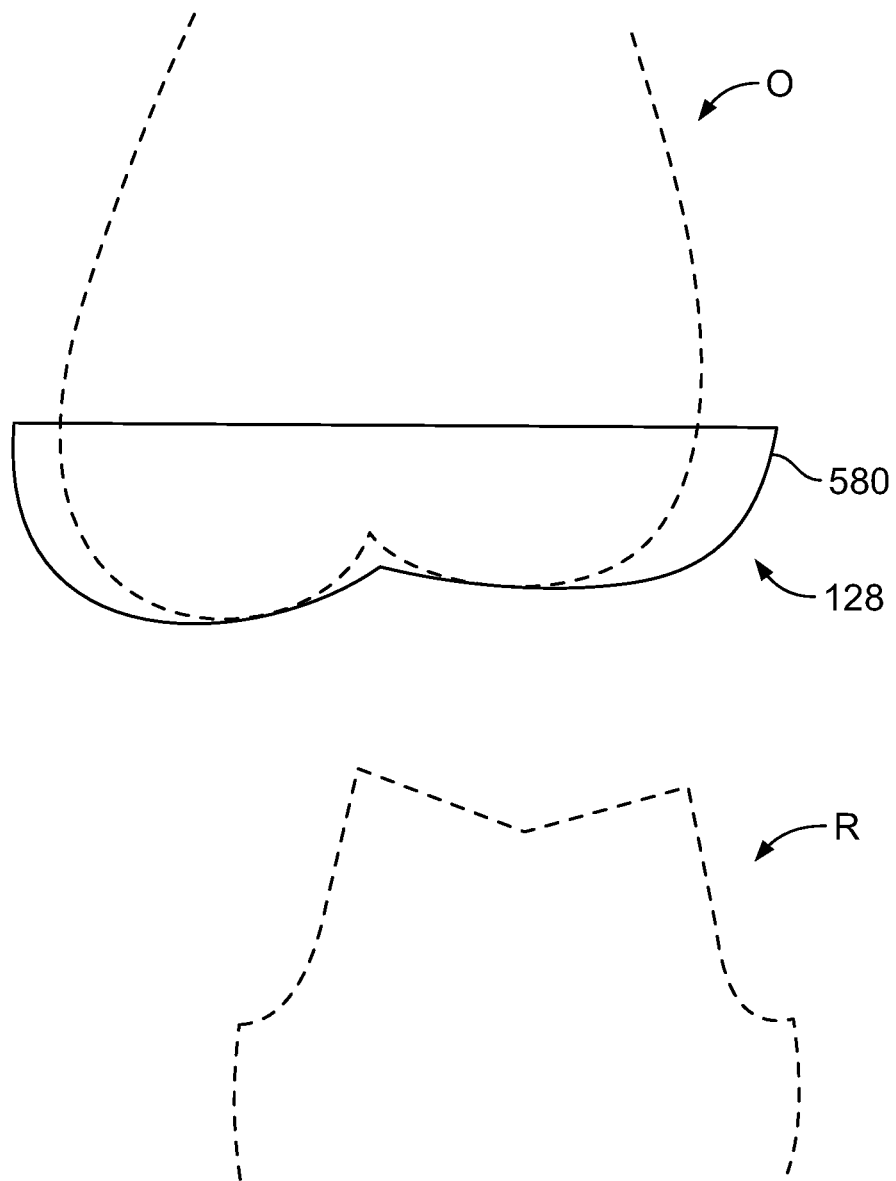
FIG. 14 is a cross-section illustration of an example interference model of FIG. 1, including an interference surface.

FIG. 14 is a cross-section illustration of an example interference model 128, including an interference surface 580. Also shown is the restoration site R and the opposing dentition O.

The interference surface 580 is a surface that is operates to indicate where a dental restoration would interfere with the opposing dentition O in at least one of the bite positions or along one of the paths between bite positions. In the example shown in FIG. 14, the interference surface 580 corresponds to the inverse of the indents 430 and 432 in the bite capture apparatus 420 shown in FIG. 10.

In some embodiments, the cross-section of the interference surface 580 is larger than the cross-section of the opposing dentition O because the interference surface 580 represents the union of the opposing dentition O in multiple bite locations. In some embodiments, the interference model 128 is used to design a dental restoration 134 for the restoration site R. For example, in some embodiments, the dental restoration 134 is designed so that it does not contact or interfere with the interference surface 580. In this manner, the dental restoration 134 will not contact or interfere with the opposing dentition O in any of the bite positions that were used to generate the interference surface 580.

Figure 15:
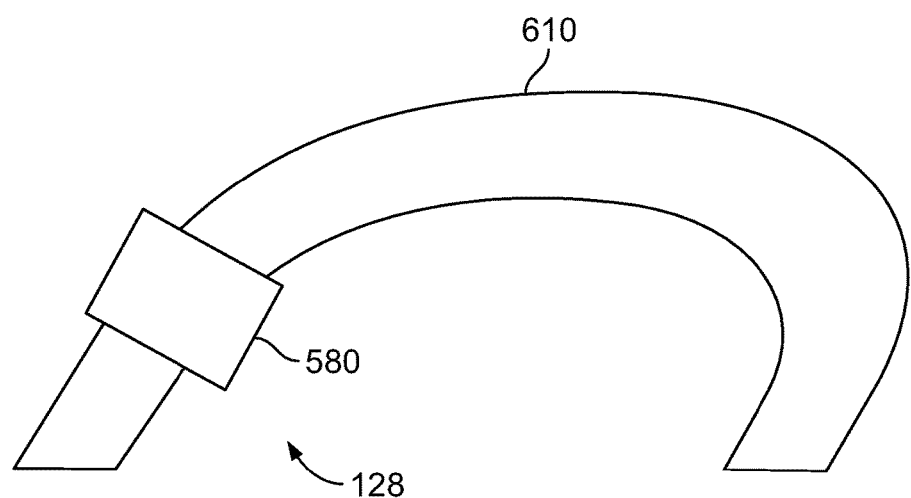
FIG. 15 is a schematic diagram of an embodiment of the interference model of FIG. 1.

FIG. 15 is a schematic diagram of an embodiment of the interference model 128. In this example, the interference model 128 includes the interference surface 580 and the retention structure 610. In this example, the interference surface 580 occupies only a portion of the dental arch. In some embodiments, the retention structure 610 is generated to follow the dental arch of the opposing dentition O. In some embodiments, the retention structure 610 comprises at least a portion of the opposing dentition O.

Figure 16:
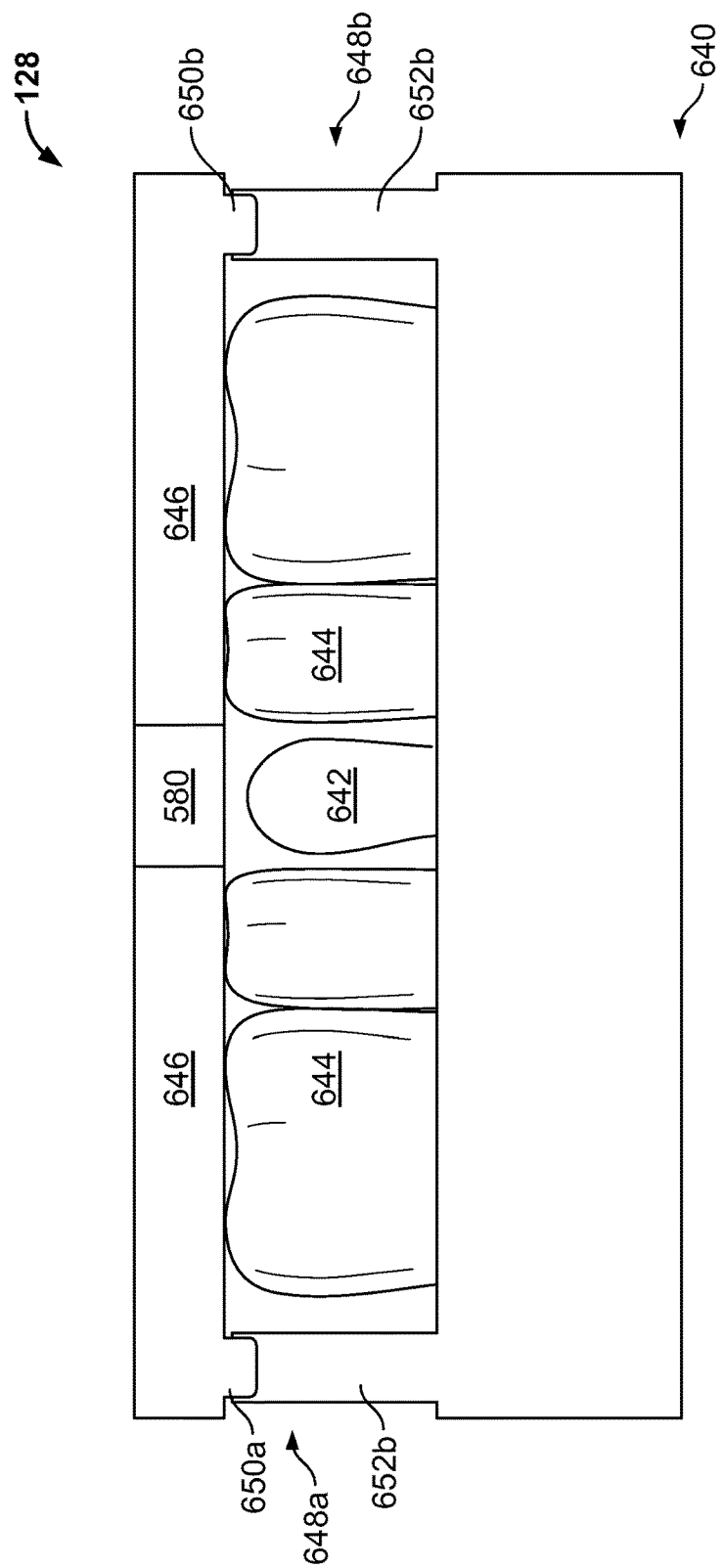
FIG. 16 is an illustration of an example embodiment of the interference model of FIG. 1 joined with a dental model.

FIG. 16 is an illustration of an example embodiment of the interference model 128 joined with a dental model 640. The interference model 128 includes the interference surface 580, and the opposing dentition surface 646. The dental model 640 includes a model 642 of the restoration site R, and a model 644 of the adjacent dentition. Also shown are retention structures 648a-b. The retention structures 648a-b are formed from lower pins 652a-b and upper pins 650a-b. The lower pins 652a-b extend from the dental model 640 and are configured to mate with the upper pins 650a-b, which extend from the interference model 128. When the lower pins 652a-b are mated with the upper pins 650a-b, the interference model 128 is properly aligned with the dental model 640. Some embodiments, include more or fewer of the retention structures 648a-b. Additionally, some embodiments, include different types of retention structures.

Figure 17:
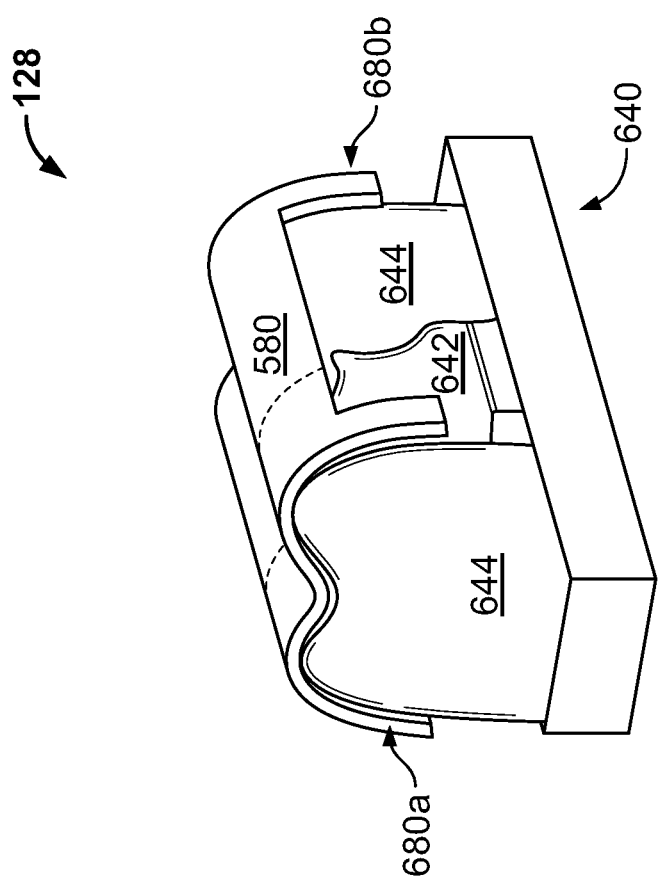
FIG. 17 is an illustration of another example embodiment of the interference model of FIG. 1 joined with a dental model.

FIG. 17 is an illustration of another example embodiment of the interference model 128 joined with a dental model 640. The interference model 128 includes the interference surface 580 and retention clips 680a-b. The retention clips 680a-b are configured to mate with the occlusal surface of the model 644 of the adjacent dentition. When the retention clips 680a-b are mated with the model 644 of the adjacent dentition, the interference model 128 is properly aligned with the dental model 640. Some embodiments, include more or fewer of the retention clips 680a-b.

Figure 18:
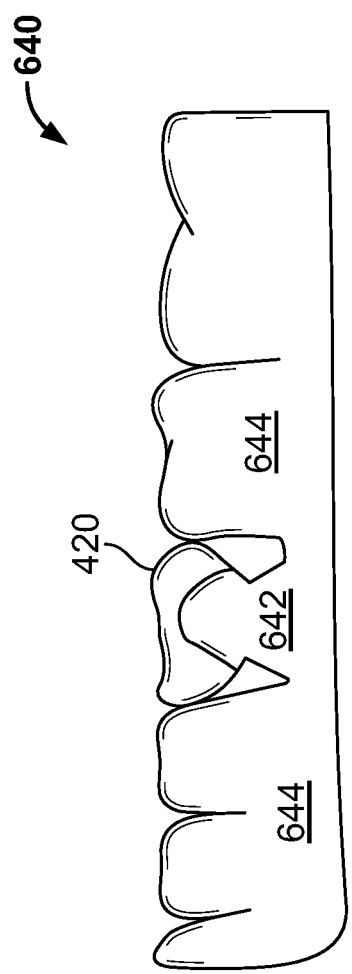
FIG. 18 is an illustration of the dental model of FIG. 16 with the bite capture apparatus of FIG. 9.

FIG. 18 is an illustration of the dental model 640. In this illustration, the bite capture apparatus 420 is also shown. The bite capture apparatus 420 is disposed on the model 642 of the restoration site. In some embodiments, the interference surface 580 (shown, for example, in FIGS. 16-17) fits snugly over the surface of the bite capture apparatus 420. In fact, in some embodiments, the bite capture apparatus 420 is disposed on the model 642 of the restoration site and scanned by the 3D scanner 116 as part of the process of generating the interference surface 580.

Figure 19:
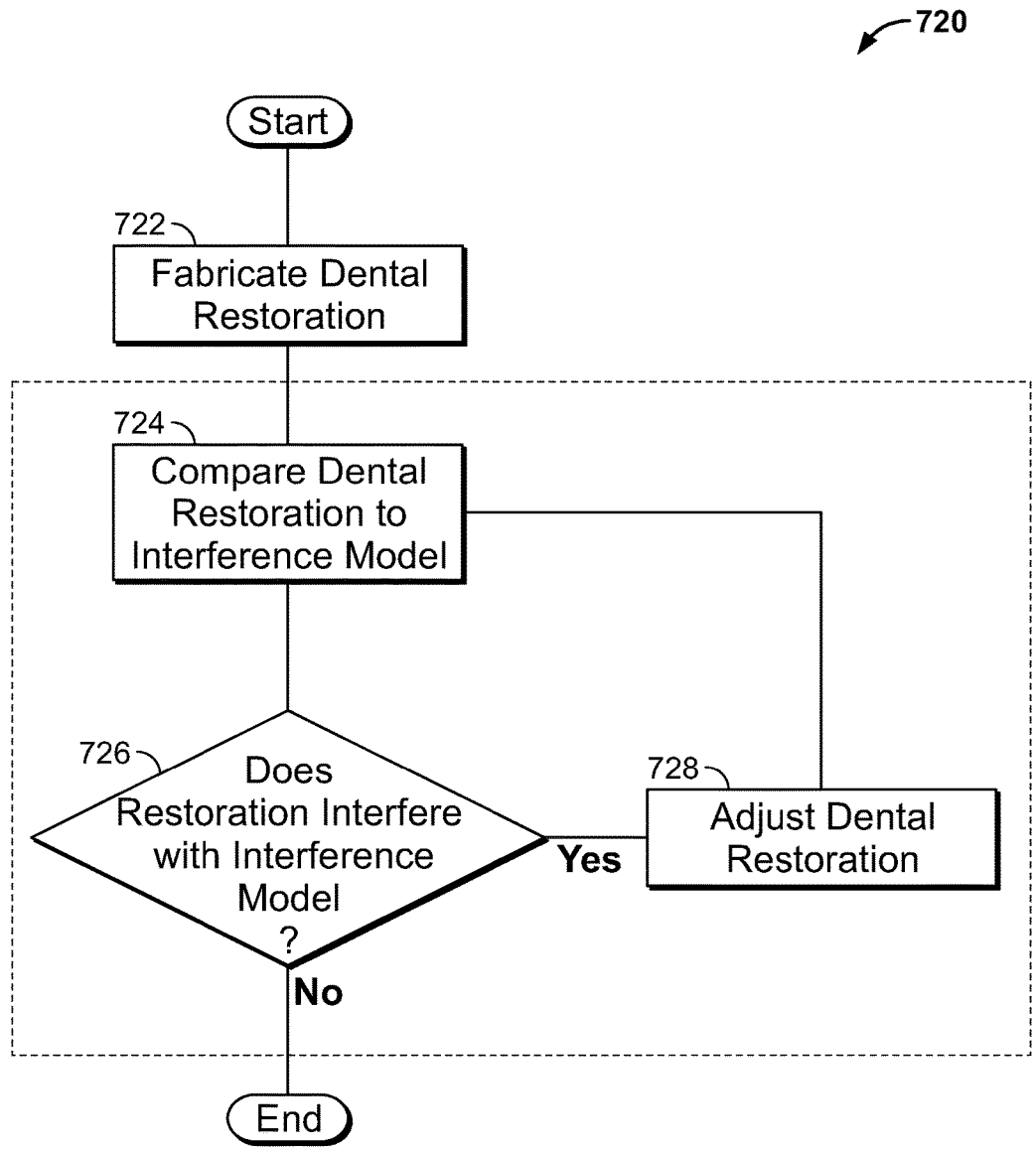
FIG. 19 is a flow chart illustrating an example method of fabricating the dental restoration using the interference model of FIG. 1.

FIG. 19 is a flow chart illustrating an example method 720 of fabricating the dental restoration 134 using the interference model 128. In some embodiments, the method 720 is performed at the restoration fabrication station 132. In this example, the method 720 includes operations 722, 724, 726, and 728.

At operation 722, the dental restoration 134 is fabricated. In some embodiments, the dental restoration 134 is designed digitally and fabricated using the rapid fabrication machine 126. In other embodiments, the dental restoration 134 is fabricated using more traditional methods, such as hand waxing and lost casting, or porcelain stacking. Additionally, in some embodiments, operation 722 is performed using the a wax-up of the dental restoration 134 rather than the dental restoration 134 itself.

At operation 724, the dental restoration 134 is compared to the interference model 128.

At operation 726, it is determined whether the dental restoration 134 interferes with the interference model 128. If so, the method 720 continues to operation 728. If not, the method 720 ends.

At operation 728, the dental restoration 134 is adjusted. After operation 728, the method returns to operation 724. This loop through operations 724-726 repeats until it is determined that the dental restoration 134 does not interfere with the interference model 128.

Figure 20:
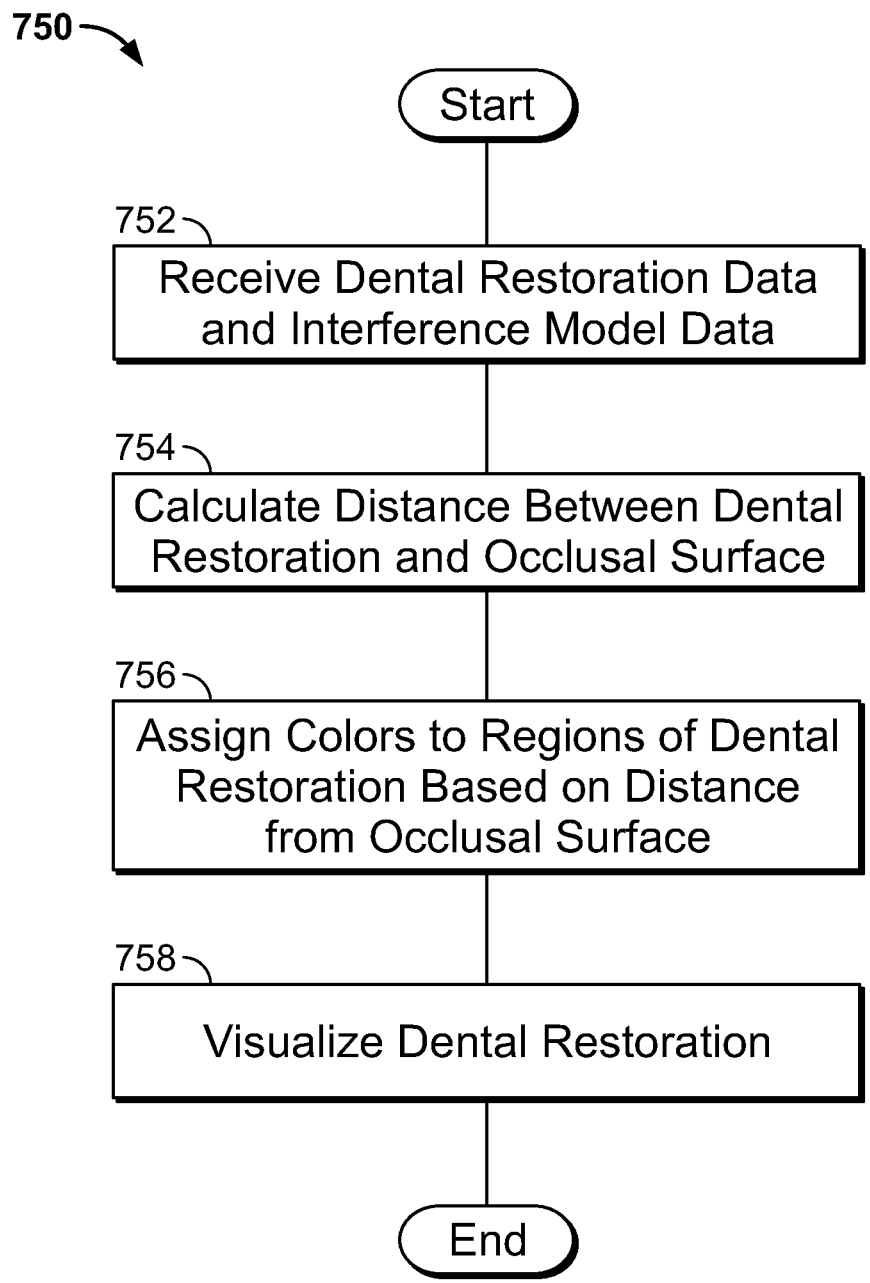
FIG. 20 is a flow chart illustrating an example method of designing the dental restoration data using the interference model data of FIG. 1.

FIG. 20 is a flow chart illustrating an example method 750 of designing the dental restoration data 124 using the interference model data 122. In some embodiments, the method 750 is performed by the design system 118. In this example, the method 750 includes operations 752, 754, 756, and 758.

At operation 752, the dental restoration data 124 and the interference model data 122 are received.

At operation 754, in some embodiments, a distance between a surface represented by the dental restoration data 124 and a surface represented by the interference model data 122 is calculated. In some embodiments, the distance is calculated by determining for each vertex on the surface represented by the dental restoration data 124 a nearest point on the surface represented by the interference model data 122 and then calculating the distance between the vertex and the point. In some embodiments, the distance is calculated as the length of a three dimensional vector between the vertex and the point. In other embodiments, the distance is calculated as the length of the projection of the three dimensional vector between the vertex and the point in the occlusal direction. In other embodiments, the distance is only calculated for vertices that intersect with surface represented by the interference model data 122. Other embodiments are possible as well.

At operation 756, in some embodiments, colors are assigned to regions of a surface represented by the dental restoration data 124 based on the distances calculated in operation 754. In some embodiments, colors are assigned to each vertex of the dental restoration data 124. In other embodiments, colors are assigned to each facet of the surface represented by the dental restoration data 124. In yet other embodiments, colors are assigned to only the facets or vertices that intersect with the surface represented by the interference model data 122. Other embodiments are possible as well.

At operation 758, the dental restorations represented by the dental restoration data 124 is visualized.

Figure 21:
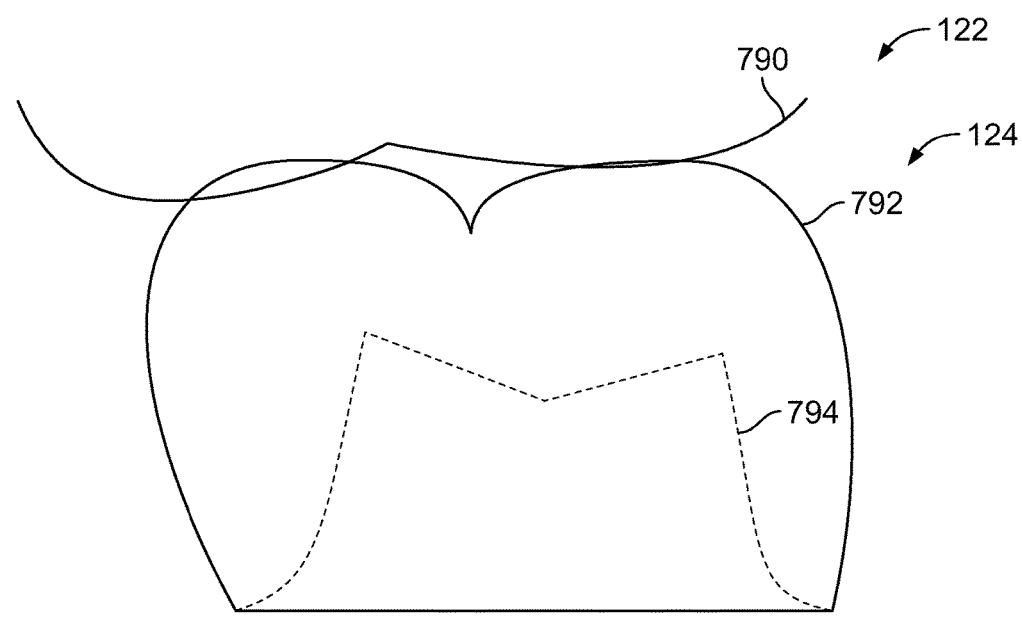
FIG. 21 is an illustration of a cross-sectional view of the interference model data and the dental restoration data of FIG. 1.

FIG. 21 is an illustration of a cross-sectional view of the interference model data 122 and the dental restoration data 124. The interference model data 122 includes an interference surface 790. The dental restoration data 124 includes an exterior surface 792 and an interior surface 794. In some embodiments, an illustration similar to FIG. 21 is displayed by a user interface of the design system 118.

The interference surface 790 is a three-dimensional surface that represents the union of the opposing dentition O in multiple bite locations.

The exterior surface 792 is a three-dimensional surface representing the exterior surface of the dental restoration 134. The interior surface 794 is a three-dimensional surface representing the interior of the dental restoration 134. In some embodiments, the interior surface 794 approximately follows the surface of the restoration site R. In some embodiments, the interior surface 794 is offset from the surface of the restoration site R by an offset amount, such as 10-200 micrometers.

In some embodiments, the interference surface 790 is compared to the exterior surface 792 to generate a color map representing the interferences between the dental restoration data 124 and the interference model data 122.

Figure 22:
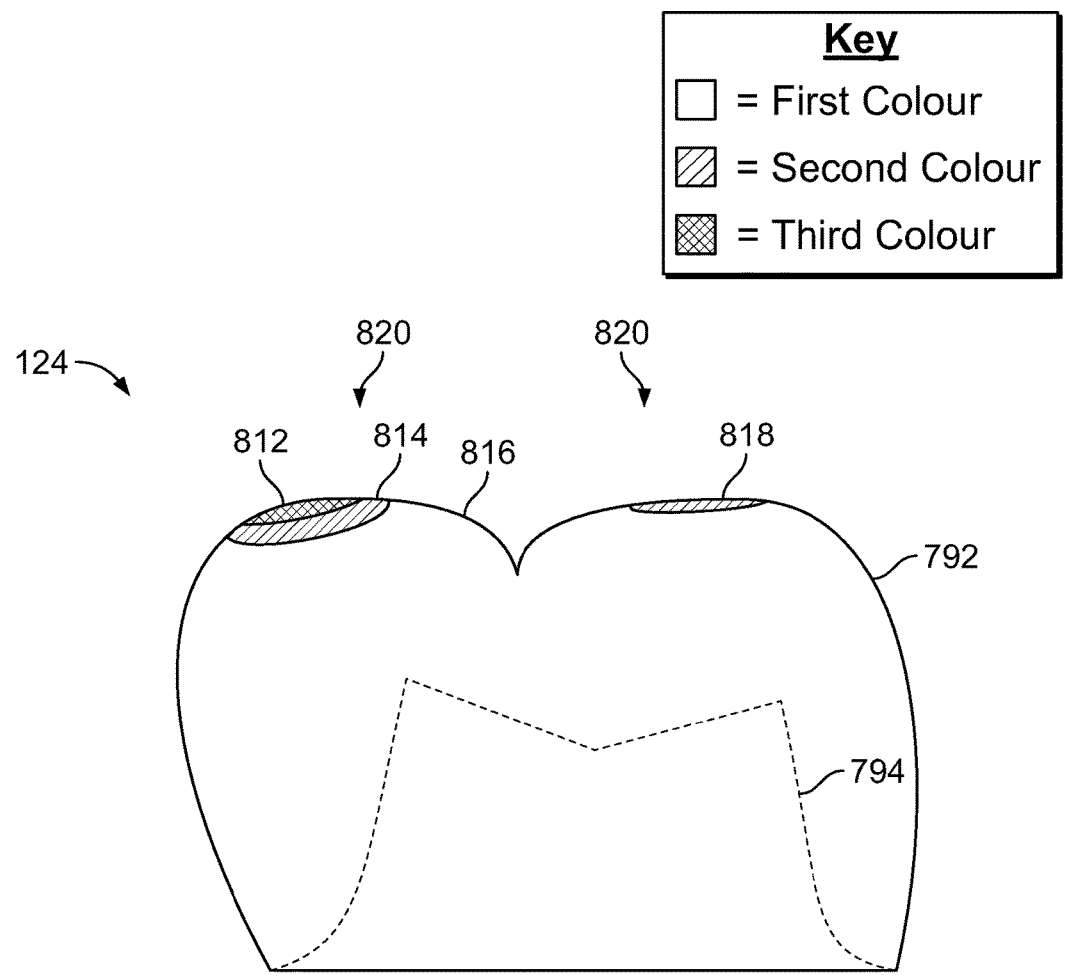
FIG. 22 is an illustration of a cross-sectional view of the dental restoration data of FIG. 1 with an example embodiment of a color map on the exterior surface.

FIG. 22 is an illustration of a cross-sectional view of the dental restoration data 124 with an example embodiment of a color map 820 on the exterior surface 792. The color map 820 includes regions 812, 814, 816, and 818. In some embodiments, the illustration in FIG. 22 is displayed by a user interface of the design system 118.

In the example shown, the regions 812, 814, 816, and 818 are displayed in different colors that represent the distance between the regions and the interference surface 790 (shown in FIG. 21). Although the embodiment shown in FIG. 22 includes four regions, other embodiments include more or fewer regions.

In the example shown, the region 812 is colored a first color. Here, the first color indicates that the region 812 interferes with the interference surface 790. For example, in some embodiments, the first color indicates that the vertices in the region 812 intersect with (i.e., are inside of) the interference surface 790. In some embodiments, the first color also indicates that the vertices are very close to interfering with the interference surface. For example, in some embodiments, the first color is used to indicate that a vertex either intersects with the interference surface 790 or is less than 10 micrometers away from the interference surface 790. In this manner, the color map 820 allows for small errors in the impressioning and scanning processes. In some embodiments, the first color is color that indicates to stop, such as red. In other embodiments, the first color is a different color.

In the example shown, the regions 814 and 818 are colored a second color. Here, the second color indicates that the regions 814 and 818 are close to interfering with the interference surface 790. For example, in some embodiments, the second color indicates that the vertices in the regions 814 and 818 are between 0 and 100 micrometers away from the interference surface 790. In some embodiments, the second color is a color that indicates to use caution, such as yellow or orange. In other embodiments, the second color is a different color.

In the example shown, the region 812 is colored a third color. Here, the third color indicates that the region 812 is not close to interfering with the interference surface 790. For example, in some embodiments, the third color indicates that the vertices in the region 812 are at least 100 micrometers away from the interference surface 790. In some embodiments, the third color is a neutral color, such as white, gray, tan, or ivory. In other embodiments, the third color is a different color.

Although, the color map 820 includes three colors, in other embodiments more or fewer colors are used. Additionally, in other embodiments, other distance ranges are used for the color map.

Figure 23:
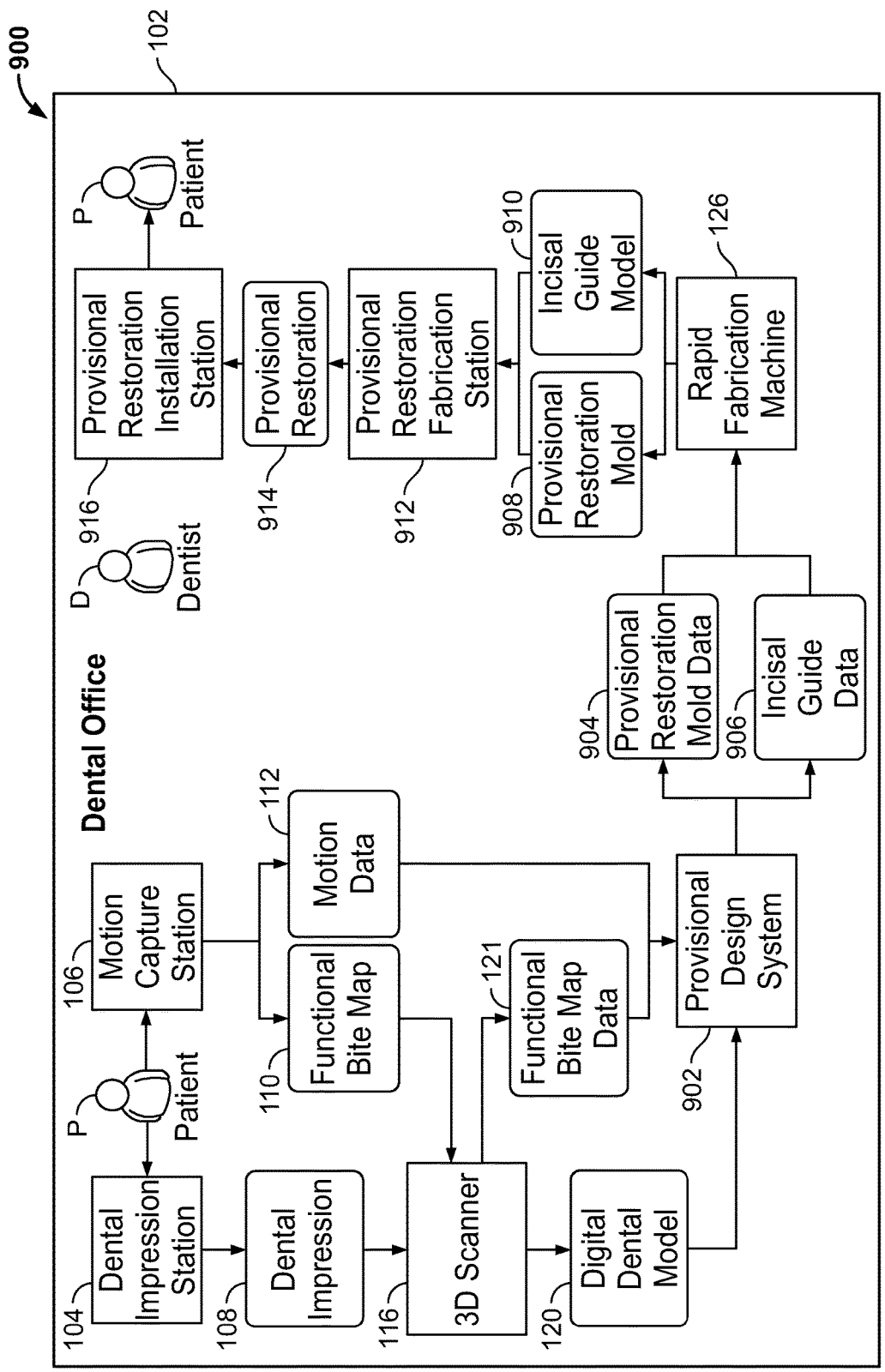
FIG. 23 is a schematic block diagram illustrating an example of a system for simulating incisal guide paths to fabricate a provisional restoration.

FIG. 23 is a schematic block diagram illustrating an example of a system 900 for simulating incisal guide paths to fabricate a provisional restoration 914. In this example, the system 900 includes a dental office 102. However, in other embodiments, the system 900 also includes a dental lab.

The example dental office 102 includes the dental impression station 104, the motion capture station 106, the 3D scanner 116, a provisional design system 902, the rapid fabrication machine 126, a provisional restoration fabrication station 912, and a provisional restoration installation station 916. Also shown are the dental impression 108, functional bite map 110, motion data 112, digital dental model 120, functional bite map data 121, provisional restoration mold data 904, incisal guide data 906, provisional restoration mold 908, incisal guide model 910, and provisional restoration 914. Additionally, the patient P and the dentist D are shown.

Although shown as a single dental office in this figure, in some embodiments, the dental office 102 comprises multiple dental offices. For example, in some embodiments, one or more of the dental impression station 104, the motion capture station 106, the 3D scanner, the provisional design system 902, the rapid fabrication machine 126, and the provisional restoration fabrication station 912 are in a different dental office than the provisional restoration installation station 916. Further, in some embodiments, one or more of the dental impression station 104, the motion capture station 106, the provisional design system 902, the rapid fabrication machine 126, the provisional restoration fabrication station 912, and the provisional restoration fabrication station 912 are not in a dental office.

The operation of the dental impression station 104, the motion capture station 106, and the 3D scanner 116 has been described with system 100 (shown in FIG. 1). These components operate in a similar manner in system 900. However, in some embodiments, one or both of the motion capture station 106 and the 3D scanner 116 are not included in the system 900. For example, in some embodiments, the digital dental model 120 is generated at the dental impression station 104 using a digital impression system. In some of these embodiments, the 3D scanner is not included. Additionally, as will be described below, some embodiments do not require the motion data 112 or the functional bite map data 121 and thus the motion capture station 106 is not included.

The provisional design system 902 is a system that is configured to generate one or both of provisional restoration mold data 904 and the incisal guide data 906. In some embodiments, the provisional restoration mold data 904 is three-dimensional digital data that represents the provisional restoration mold 908 and is in a format suitable for fabrication using the rapid fabrication machine 126. Similarly, in some embodiments, the incisal guide data 906 is three-dimensional digital data that represents the incisal guide model 910 and is in a format suitable for fabrication using the rapid fabrication machine 126.

In some embodiments, the provisional design system 902 comprises a computing device including user input devices. In some embodiments, the provisional design system 902 includes computer-aided-design (CAD) software that generates a graphical display of one or both of the provisional restoration mold data 904 and the incisal guide data 906 and allows an operator to interact with and manipulate one or both of the provisional restoration mold data 904 and the incisal guide data 906. In some embodiments, the provisional design system 902 comprises digital tools that mimic the tools used by a laboratory technician to physically design a provisional dental restoration. In some other embodiments, the provisional design system 902 comprises a server that partially or fully automates the generation of designs of one or both of the provisional restoration mold data 904 and the incisal guide data 906.

In some embodiments, the provisional restoration mold 908 is used at the provisional restoration fabrication station 912 to fabricate the provisional restoration 914. In some embodiments, the provisional restoration fabrication station 912 and the provisional restoration installation station 916 are integrated and the provisional restoration mold 908 is used to fabricate the provisional restoration 914 in the mouth of the patient P. In other embodiments, the incisal guide model 910 is used at the provisional restoration fabrication station 912 to fabricate the provisional restoration 914 on an articulator.

In some embodiments, the provisional restoration 914 is seated in the mouth of the patient P in the provisional restoration installation station 916 by the dentist D.

Figure 24:
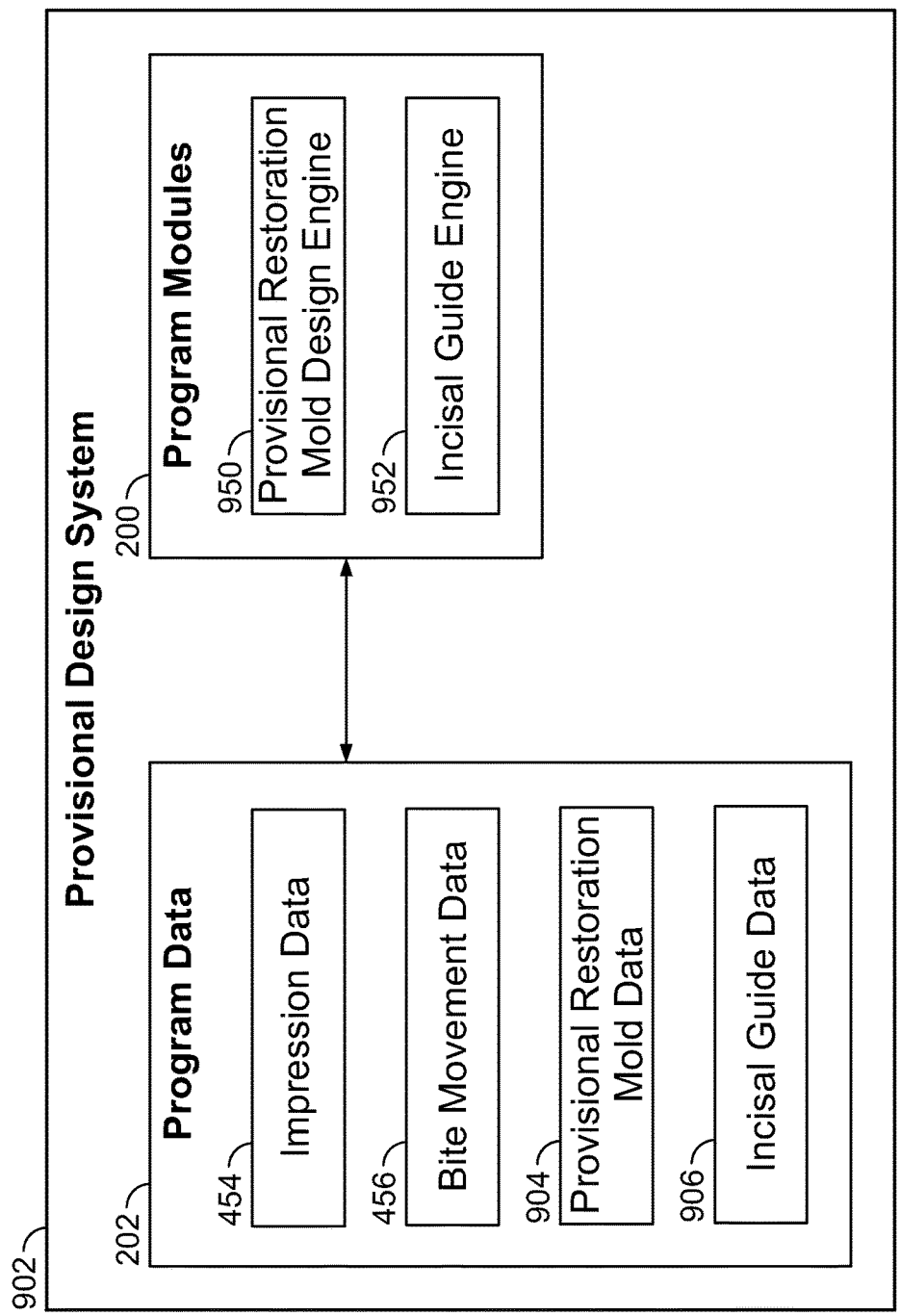
FIG. 24 illustrates an exemplary architecture of the program modules and the program data of the provisional design system of FIG. 23.

FIG. 24 illustrates an exemplary architecture of the program modules 200 and program data 202 of the provisional design system 902. The program modules 200 include a plurality of modules that, when executed by the processing device 180 (shown in FIG. 2), perform one or more operations of the provisional design system 902. The modules include a provisional restoration mold design engine 950 and an incisal guide engine 952. In some embodiments, the program modules 200 includes more, fewer, or different modules than those shown in FIG. 24.

The program data 202 is stored in a data storage device, such as the memory 182 or the secondary storage device 192 (shown in FIG. 2). In some embodiments, program data 202 includes impression data 454, bite movement data 456, provisional restoration mold data 904, and incisal guide data 906. In some embodiments, the program data 202 include more, fewer, or different types of data than the data shown in FIG. 9.

In some embodiments, the data stored in program data 202 can be represented in one or more files having any format usable by a computer. Examples include text files formatted according to a markup language and having data items and tags to instruct computer programs and processes how to use and present the data item. Examples of such formats include html, xml, and xhtml, although other formats for text files can be used. Additionally, the data can be represented using formats other than those conforming to a markup language.

The provisional restoration mold design engine 950 operates to generate the provisional restoration mold data 904. In some embodiments, the provisional restoration mold design engine 950 uses the impression data 454 and the bite movement data 456 to generate the provisional restoration mold data 904.

The incisal guide engine 952 operates to generate the incisal guide data 906. In some embodiments, the incisal guide engine 952 uses the impression data 454 and the bite movement data 456 to generate the incisal guide data 906.

Figure 25:
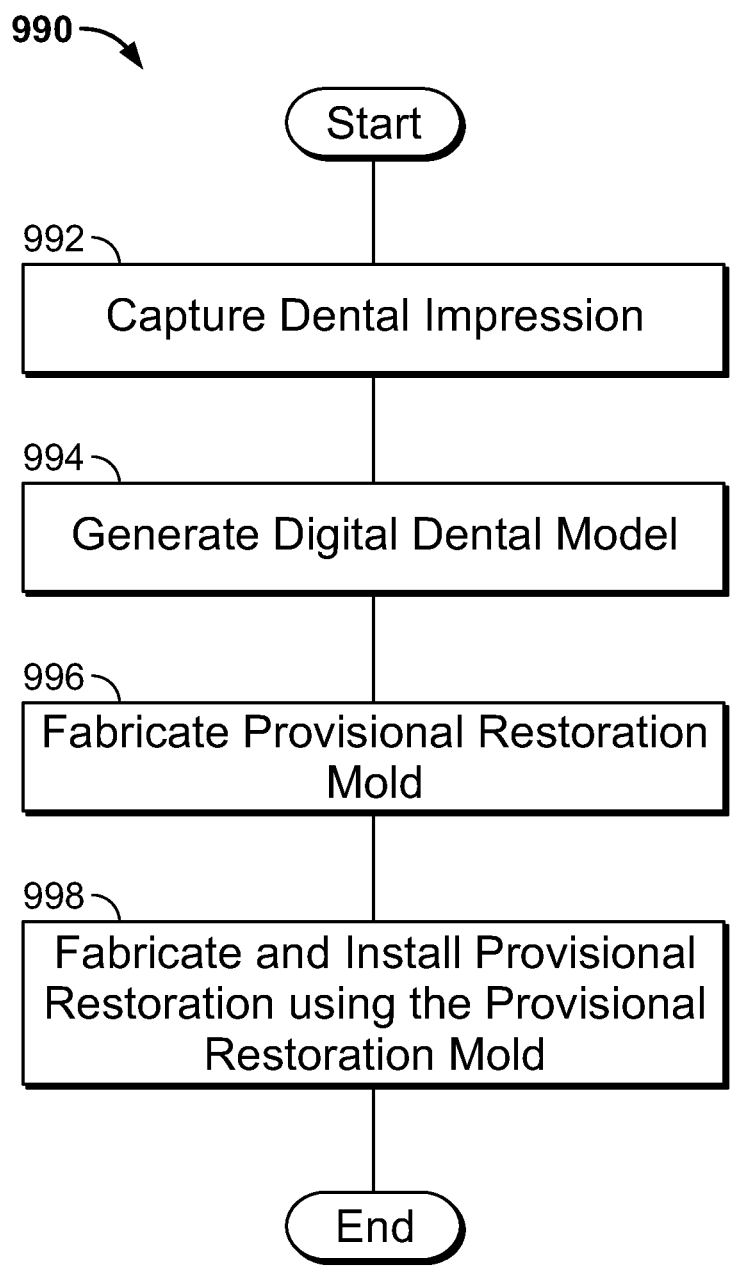
FIG. 25 is a flow chart illustrating an example method of using the system of FIG. 23 to fabricate and install the provisional restoration.

FIG. 25 is a flow chart illustrating an example method 990 of using the system 900 to fabricate and install the provisional restoration 914. In some embodiments, the method 990 is performed in the dental office 102. In other embodiments, the method 990 is performed in multiple locations, such as one or more dental offices and dental laboratories. In this example, the method 990 includes operations 992, 994, 996, and 998.

At operation 992, the dental impression 108 is captured. At operation 994, the digital dental model 120 is generated. In some embodiments, the digital dental model 120 is generated by using the 3D scanner 116 to scan the dental impression 108. In other embodiments, the dental impression station 104 generates the digital dental model 120 directly.

At operation 996, the provisional restoration mold 908 is fabricated. In some embodiments, the provisional restoration mold 908 is fabricated by the rapid fabrication machine 126 using the provisional restoration mold data 904. In some embodiments, the provisional restoration mold data 904 is generated by the provisional design system 902 using the digital dental model 120. In some embodiments, the provisional design system 902 also uses one or both of the functional bite map data 121 and motion data 112 to generate the provisional restoration mold data 904.

At operation 998, the provisional restoration 914 is fabricated and installed in the patient P's mouth using the provisional restoration mold 908. In some embodiments, the provisional restoration 914 is fabricated by filling the provisional restoration mold 908 with a provisional material such as an acrylic resin or bis-acrylic. Some examples of acrylic resins include polymetheyl methacrylate and polyethyl methacrylate. In some embodiments, other materials are used as well.

In some embodiments, once the provisional restoration mold 908 is filled with the provisional material, the provisional restoration mold 908 is placed over the restoration site in the patient P's mouth. In some embodiments, the provisional restoration mold 908 is aligned with the restoration site using landmarks or contours of adjacent teeth. After the provisional material has hardened, the provisional restoration mold 908 is removed. In some embodiments, the dentist D adjusts and polishes the provisional material to finish the provisional restoration 914.

Figure 26:
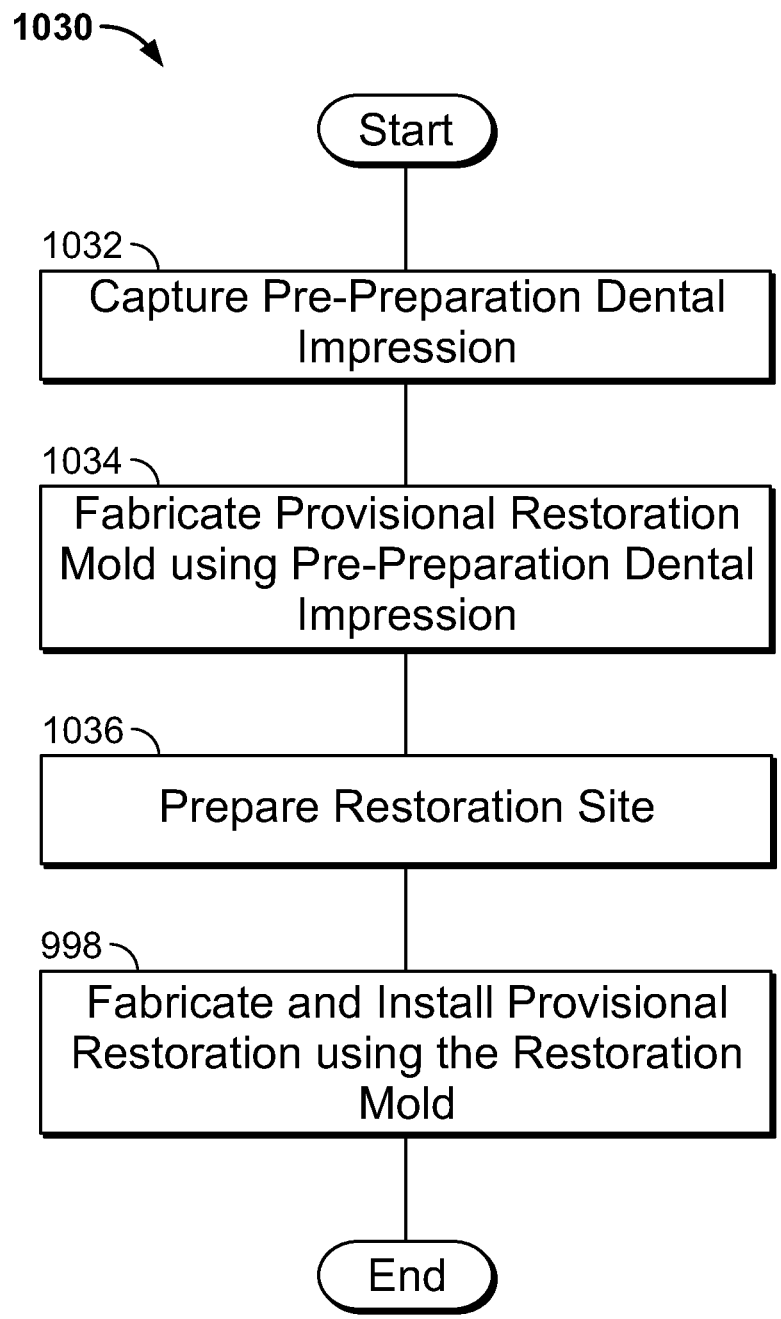
FIG. 26 is a flow chart illustrating another example method of using the system of FIG. 23 to fabricate and install the provisional restoration.

FIG. 26 is a flow chart illustrating another example method 1030 of using the system 900 to fabricate and install the provisional restoration 914. In some embodiments, the method 1030 is performed in the dental office 102. In other embodiments, the method 1030 is performed in multiple locations, such as one or more dental offices and dental laboratories. In this example, the method 1030 includes operations 1032, 1034, 1036, and 998.

At operation 1032, the pre-preparation dental impression is captured. The pre-preparation dental impression represents the dentition of the patient P before the dentist has prepared the restoration site for the provisional restoration 914. In some embodiments, the pre-preparation dental impression provides information regarding the proper anatomy and contour of the provisional restoration 914. The pre-preparation dental impression can be captured using any digital or physical impression techniques that are used to capture dental impressions.

At operation 1034, the provisional restoration mold 908 is fabricated using the pre-preparation dental impression. In some embodiments, the interior surface of the provisional restoration mold 908 is fabricated to match the surface of the pre-preparation dentition at the restoration site. Additionally, in some embodiments, the interior surface of the provisional restoration mold 908 is fabricated to match the surface of the pre-preparation dentition with an offset. For example, in some embodiments, the interior surface of the provisional restoration mold 908 is offset from the surface of the pre-preparation dentition by 20-100 micrometers.

Additionally, in some embodiments, the interior surface of the provisional restoration mold 908 is shifted in the vertical dimension by an amount corresponding to a desired change in the vertical dimension of occlusion of the patient's dentition. The vertical dimension of occlusion refers to the distance between the maxilla and mandible when in maximum intercuspation.

In some embodiments, the dentist D may desire to increase the vertical dimension of occlusion of the patient P by 1 mm. The dentist D may accomplish this by increasing the height of the dentition at one more of the contact locations during maximum intercuspation using one or more restorations. Conversely, the dentist D may desire to lower the vertical dimension of occlusion of the P by 1 mm instead. The dentist D may accomplish this by removing dentition to lower the height of one or more of the contact locations during maximum intercuspation. In either case, in some embodiments, the interior surface of the provisional restoration mold is shifted by a corresponding amount in the vertical dimension as well. In this manner, the contour of the provisional restoration 914 matches the original contour and is located in the same position relative to the opposing dentition even after the vertical dimension of occlusion is adjusted.

At operation 1036, the dentist D prepares the restoration site. In some embodiments, the dentist D prepares the restoration site by removing some of the structure of the patient P's dentition so that the restoration site is prepared to receive a dental restoration.

Next, at operation 998, the provisional restoration 914 is fabricated and installed in the patient P's mouth using the provisional restoration mold 908.

Figure 27:
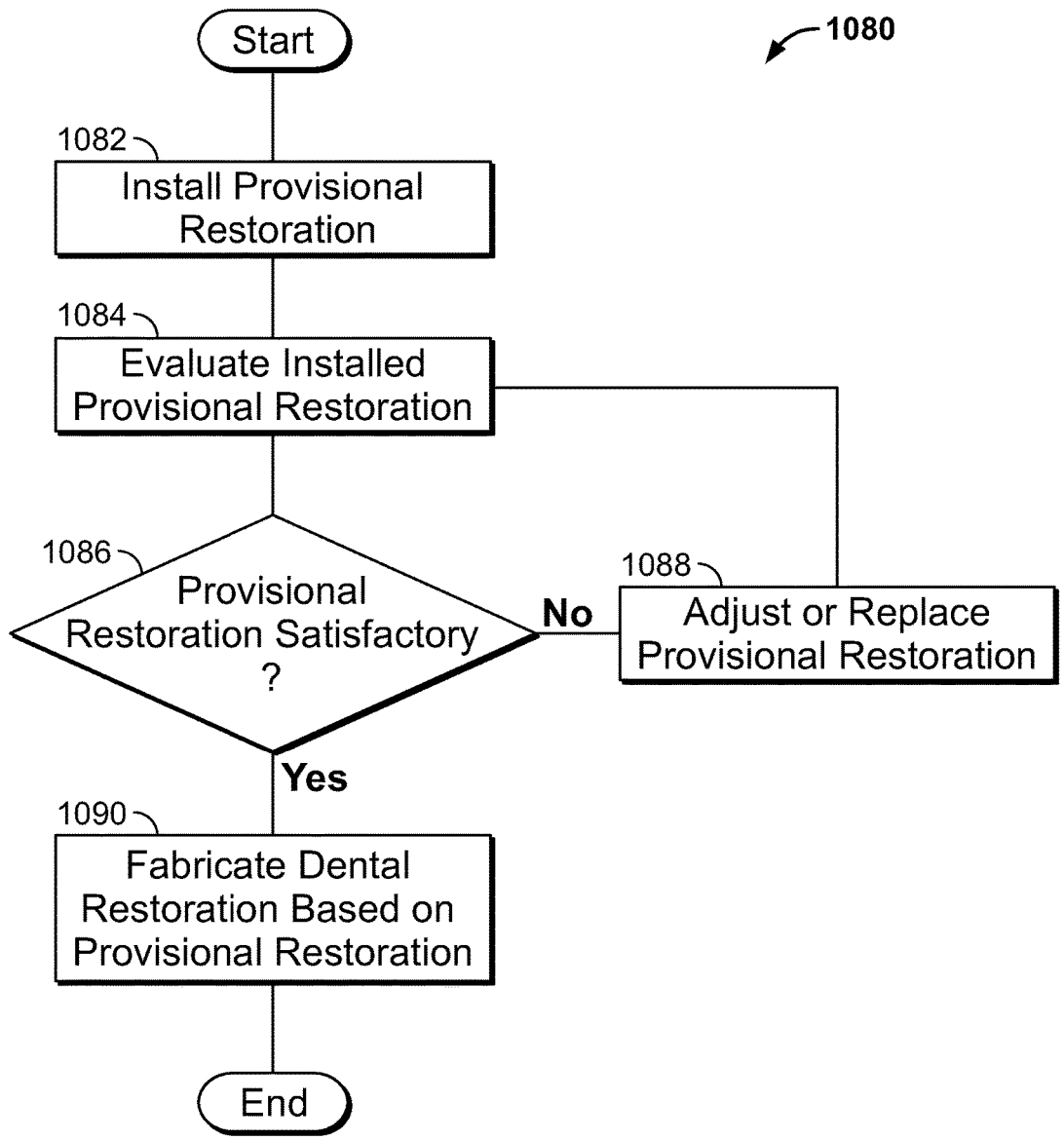
FIG. 27 is a flow chart illustrating an example method of using the system of FIG. 23 to fabricate a dental restoration based on the provisional restoration.

FIG. 27 is a flow chart illustrating an example method 1080 of using the system 900 to fabricate a dental restoration based on the provisional restoration 914. In some embodiments, the method 1080 is performed in the dental office 102. In other embodiments, the method 1080 is performed in multiple locations, such as one or more dental offices and dental laboratories. In this example, the method 1080 includes operations 1082, 1084, 1086, and 1088.

At operation 1082 the provisional restoration 914 is installed in the patient P. In some embodiments, the provisional restoration 914 is fabricated and installed using the method 1030 (shown in FIG. 26). In other embodiments, the provisional restoration 914 is fabricated using the method 990 (shown in FIG. 25). In other embodiments, the provisional restoration 914 is fabricated using other methods.

At operation 1084, the provisional restoration 914 is evaluated in the patient P's mouth. In some embodiments, the patient P wears the provisional restoration 914 for an evaluation time period and provides feedback to the doctor D. Additionally, in some embodiments, the doctor D inspects the provisional restoration 914 for signs of wear after the evaluation time period.

At operation 1086, it is determined whether the provisional restoration 914 is satisfactory. In some embodiments, the doctor D determines whether the provisional restoration 914 is satisfactory based on the evaluation of operation 1084. If the provisional restoration 914 is satisfactory, the method 1080 continues to operation 1090. If the provisional restoration 914 is not satisfactory the method 1080 continues to operation 1088.

At operation 1088, the provisional restoration 914 is adjusted or replaced. In some embodiments, the provisional restoration 914 is adjusted using an abrasive wheel or another carving tool without being removed from the patient P's mouth. In other embodiments, the provisional restoration mold data 904 is adjusted using the provisional design system 902. In these embodiments, the provisional restoration mold data 904 is adjusted based on the evaluation of operation 1084. Then, the provisional restoration mold 908 is fabricated by the rapid fabrication machine 126 using the provisional restoration mold data 904 after it has been adjusted. Then, the provisional restoration mold 908 is used to fabricate and install a new provisional restoration. After the provisional restoration 914 is adjusted or replaced, the method 1080 returns to operation 1084 so that the new provisional restoration can be evaluated.

At operation 1090, a dental restoration is fabricated based on the provisional restoration 914. In some embodiments, the dental restoration is fabricated using data acquired by scanning the provisional restoration 914 with the 3D scanner 116. In other embodiments, the dental restoration is fabricated using the provisional restoration mold data 904. In some embodiments, one or both of the provisional restoration mold data 904 and the data acquired by scanning the provisional restoration 914 are used by the design system 118 (shown in FIG. 1) to design the dental restoration data 124. The dental restoration data 124 is then used to fabricate the dental restoration 134.

Figure 28:
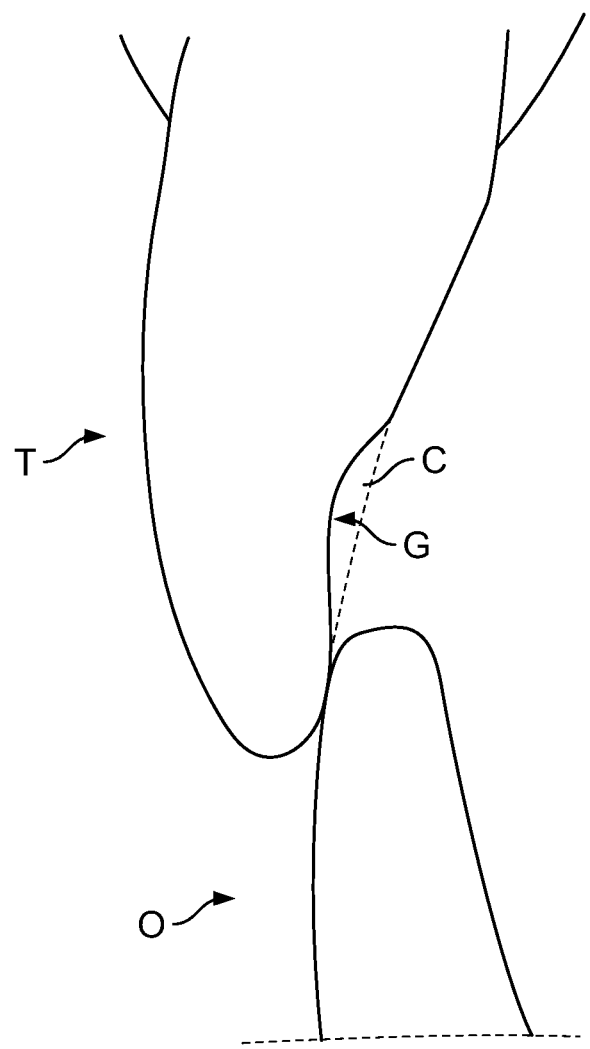
FIG. 28 is a cross-sectional illustration of the anterior dentition of the patient.

FIG. 28 is a cross-sectional illustration of the anterior dentition of the patient P. The tooth T and the opposing dentition O are shown. The tooth T represents a tooth that the dentist D intends to replace or repair with a restoration. The opposing dentition O represents the opposing tooth or teeth on the opposite arch of the tooth T.

Also shown is the original contour C and the incisal guide path G. The original contour C represents the surface of the tooth T prior to being worn away by the opposing dentition O. The incisal guide path G represents the worn surface of the tooth T.

In some embodiments, the shape of the incisal guide path G is preserved when the tooth T is replaced by the provisional restoration 914 or the dental restoration 134. In some embodiments, by preserving the incisal guide path G the provisional restoration 914 and the dental restoration 134 fit more harmoniously with the opposing dentition O and are less likely to fracture due to wear from the opposing dentition O. In some embodiments, the provisional restoration mold 908 is fabricated with an interior contour that preserves the incisal guide path G.

Figure 29:
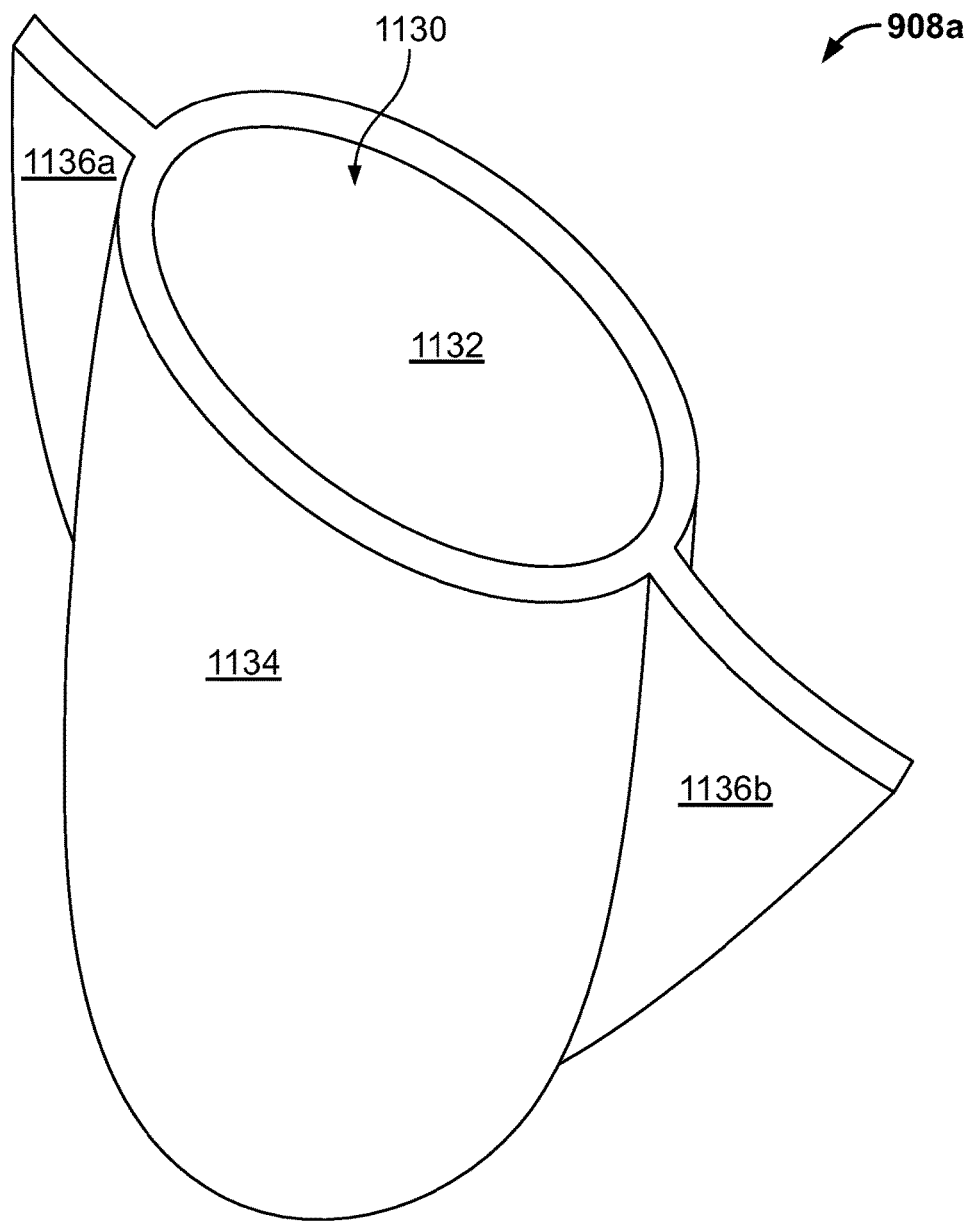
FIG. 29 is an illustration of an example of an embodiment of the provisional restoration mold of FIG. 23.

FIG. 29 is an illustration of an example of an embodiment 908a of the provisional restoration mold 908. The provisional restoration mold 908a includes an interior surface 1130, including incisal guide path surface 1132, exterior surface 1134, and registration structures 1136a-b, including registration surfaces 1138a-b. In some embodiments, the provisional restoration mold 908a is formed from a biocompatible material that is safe for temporary in-mouth placement. For example, in some embodiments, the provisional restoration mold 908a is formed by the rapid fabrication machine 126 from an acrylic material such as Object MED610, available from STRATSYS LTD. of Eden Prairie, Minn.

The interior surface 1130 operates to define the shape of some or all of the exterior surface of the provisional restoration 914. In some embodiments, the incisal guide path surface 1132 matches the contour of the incisal guide path G. In some embodiments, the incisal guide path surface 1132 is offset vertically to compensate for an adjustment to the patient P's vertical dimension of occlusion.

The exterior surface 1134 is offset from the interior surface 1130 to form the walls of the provisional restoration mold. In some embodiments, the exterior surface 1134 is offset from the interior surface 1130 uniformly to generate walls with substantially uniform thickness. In other embodiments, the exterior surface 1134 is offset from the interior surface 1130 non-uniformly to generate walls with a non-uniform thickness. For example, in some embodiments, the exterior surface 1134 is offset from the interior surface 1130 by a smaller distance in the interproximal walls than on the labial and lingual walls of the provisional restoration mold 908a.

The registration structures 1136a-b operate to align the provisional restoration mold 908a. In some embodiments, the registration surfaces 1138a-b match the labial surfaces of the dentition adjacent to the restoration site. In some embodiments, the registration surfaces 1138a-b are configured to be fit against a specific portion of the labial surfaces of the dentition adjacent to the restoration site. In this manner, the dentist D can determine that the provisional restoration mold 908a is properly aligned with the prep site when the registration surfaces 1138a-b fit properly against the dentition adjacent to the restoration site. Although two of the registration structures 1136a-b are included in the embodiment of the provisional restoration mold 908a shown in FIG. 29, in other embodiments more or fewer registration structures are included. Additionally, in some embodiments, other registration structures are used to align the provisional restoration mold 908a with the restoration site.

Figure 30:
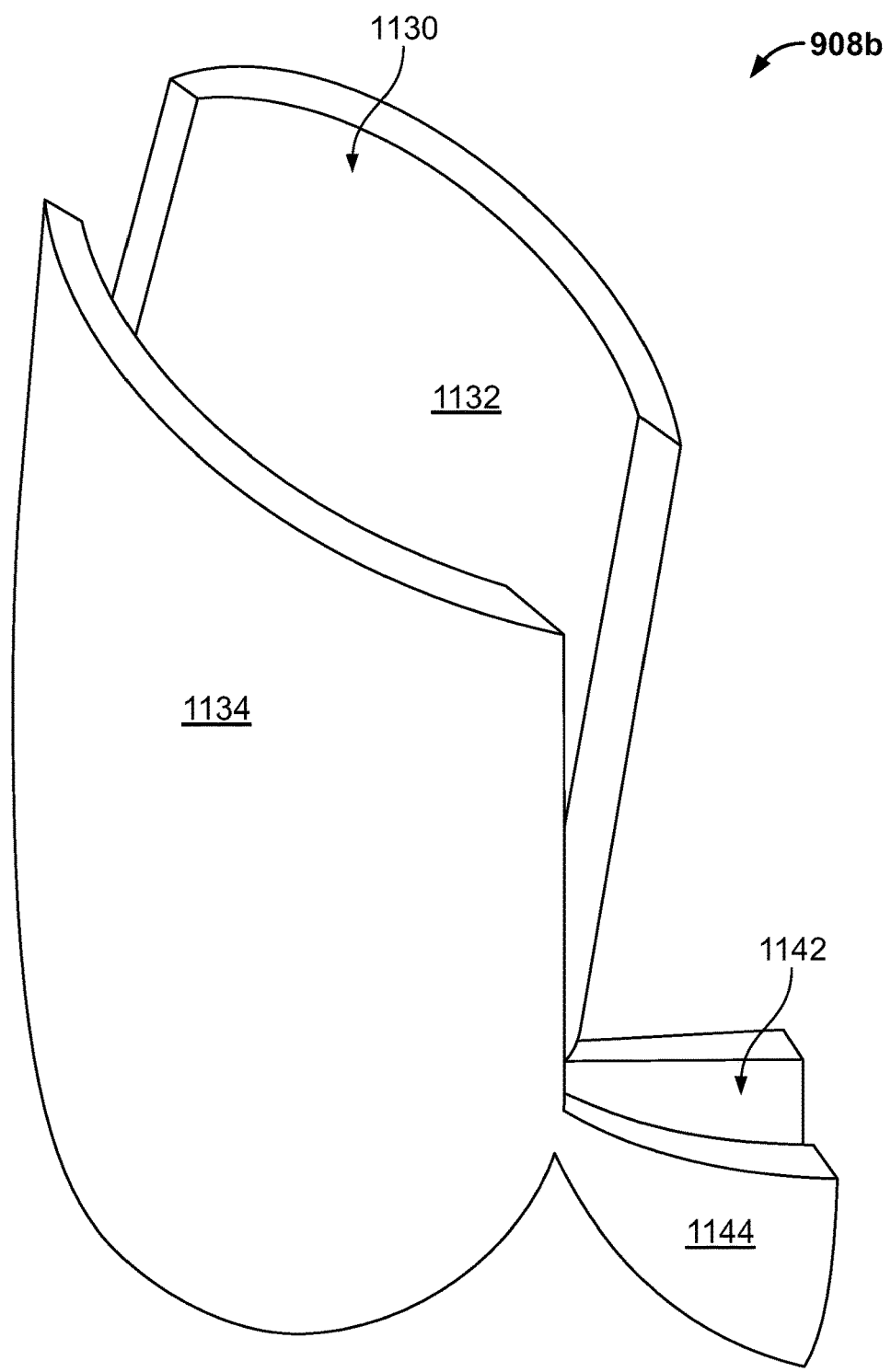
FIG. 30 is an illustration of an alternative embodiment of the provisional restoration mold of FIG. 23.

FIG. 30 is an illustration of an alternative embodiment 908b of the provisional restoration mold 908. The embodiment shown in FIG. 30 is similar to the embodiment 908a shown in FIG. 29.

The embodiment shown in FIG. 30 includes a registration structure 1142, including registration surface 1144. Additionally, the interior surface 1130 and the exterior surface 1134 do not fully surround the restoration site. Instead, the interior surface 1130 and the exterior surface 1134 are open along the proximal walls. In some embodiments, this allows the provisional restoration to be formed in contact with the adjacent dentition.

The registration structure 1142 is a physical structure configured to align the provisional restoration mold 908b with the restoration site. In some embodiments, the registration surface 1144 matches the incisal edge of the adjacent dentition. In this manner, the dentist D can determine that the provisional restoration mold 908b is properly aligned with restoration site when the provisional restoration mold is fully seated on the adjacent dentition. Although only one registration structure 1142 is shown in FIG. 30, other embodiments include additional registration structures.

Figure 31:
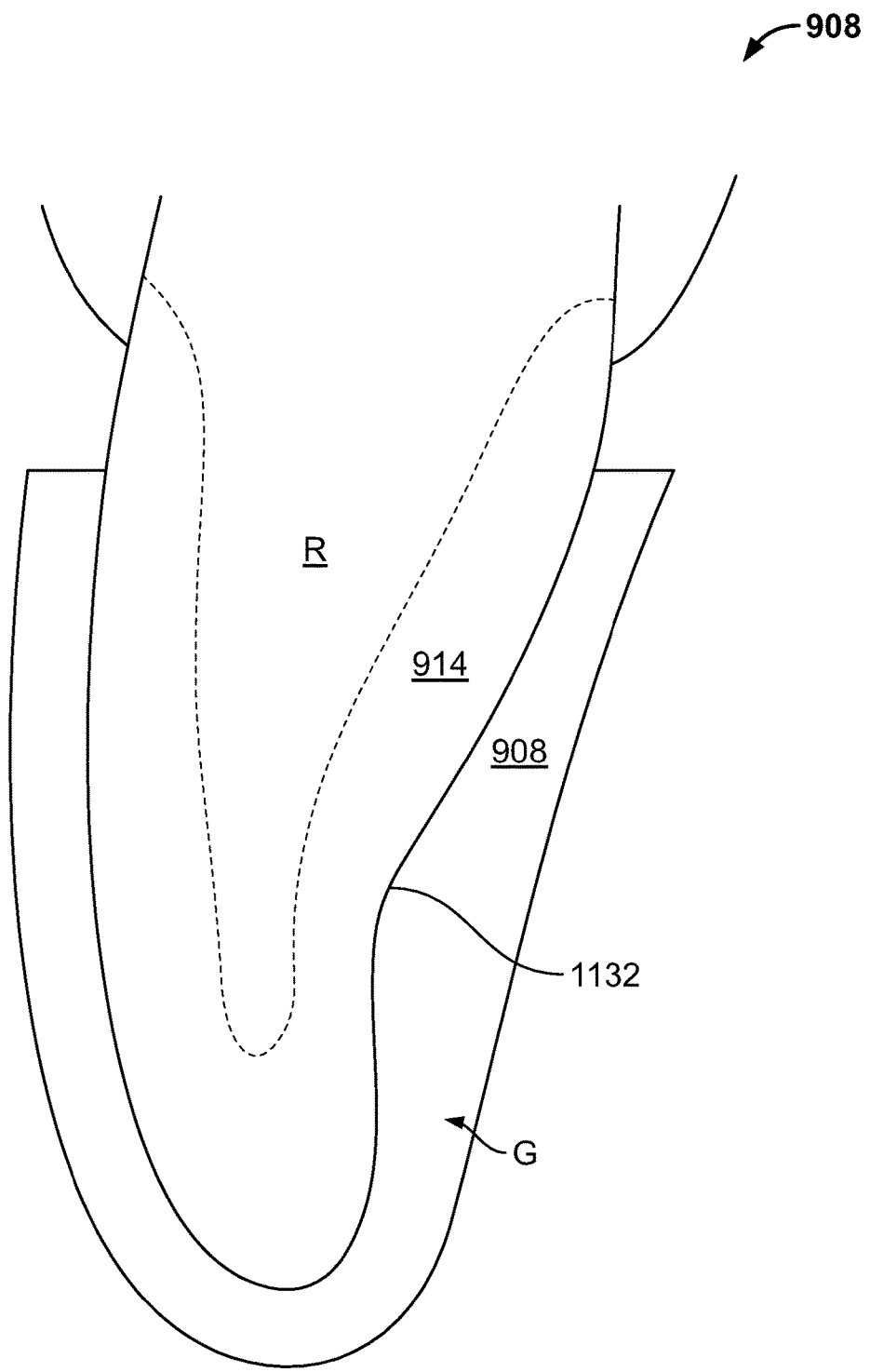
FIG. 31 is a cross-sectional illustration of a provisional restoration mold of FIG. 23 being used to form a provisional restoration on a restoration site R.

FIG. 31 is a cross-sectional illustration of a provisional restoration mold 908 being used to form a provisional restoration 914 on a restoration site R. As shown in this figure, the incisal guide path surface 1132 of the provisional restoration mold 908 generates an incisal guide path G on the provisional restoration 914 that matches the original incisal guide path.

Figure 32:
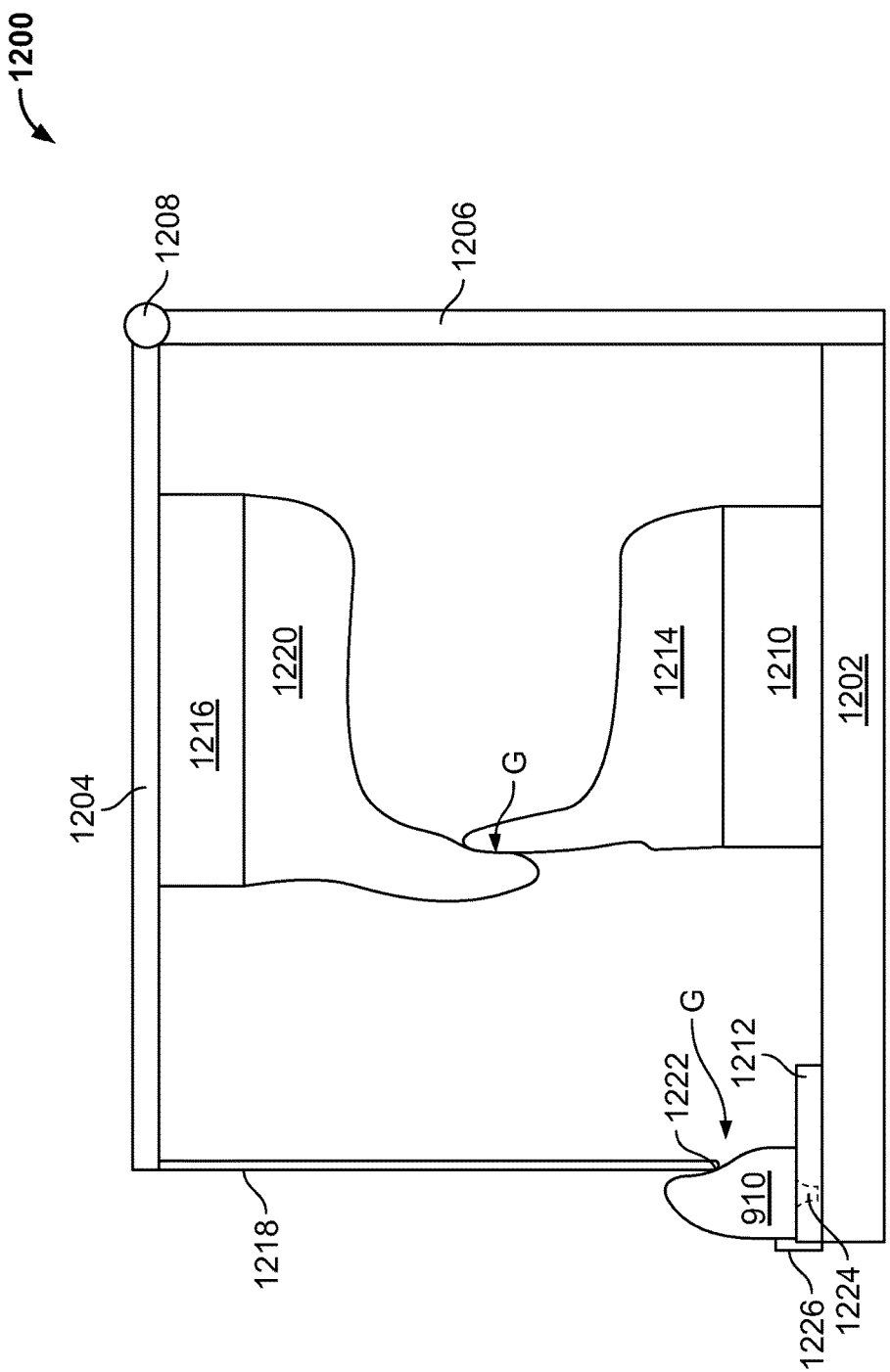
FIG. 32 is a cross-sectional illustration of an articulator being used with an incisal guide model of FIG. 23.

FIG. 32 is a cross-sectional illustration of an articulator 1200 being used with an incisal guide model 910. In some embodiments, the articulator 1200 includes a lower structure 1202, an upper structure 1204, and a vertical support 1206, including a socket 1208.

The lower structure 1202 is a rigid structure and includes a lower model mounting plate 1210 and an incisal guide model mounting plate 1212. The lower model mounting plate 1210 operates to secure a lower arch dental model 1214 to the articulator 1200. The incisal guide model mounting plate 1212 operates to secure an incisal guide model 910 to the articulator 1200.

The upper structure 1204 is a rigid structure and includes an upper model mounting plate 1216 and a guide pin 1218. The upper model mounting plate 1216 operates to secure an upper arch dental model 1220 to the articulator 1200. The guide pin 1218 is a rigid structure that includes a tip 1222. The guide pin 1218 is rigidly secured to the upper structure 1204 and is configured to be immovable relative to the upper structure 1204 during operation of the articulator 1200. The tip 1222 of the guide pin 1218 is configured to move along the surface of the incisal guide model 910. As the guide pin 1218 moves along the surface of the incisal guide model 910, the upper structure 1204 and the upper arch dental model 1220 move in a manner that replicates the motion of the patient P's jaw.

The vertical support 1206 is a rigid structure that is rigidly coupled to the lower structure 1202 and is configured to be immovable relative to the lower structure 1202 during operation of the articulator 1200. The vertical support 1206 includes a socket 1208. The socket is configured to couple with the upper structure 1204. In some embodiments, the socket 1208 is configured to allow the upper structure 1204 to rotate and move while remaining coupled. In this manner, the socket 1208 approximates the condyle of the patient's jaw.

The incisal guide model 910 is a model that forms a surface that corresponds to the incisal guide path G. In some embodiments, as the guide pin 1218 moves across the surface of the incisal guide model 910, the upper arch dental model 1220 moves relative to the lower arch dental model 1214 in a manner that is similar to the actual motion of the patient P's jaw. In some embodiments, as the guide pin 1218 moves across the incisal guide model 910, a surface of the upper arch dental model 1220 that corresponds to the incisal guide path G contacts the lower arch dental model 1214. In this manner, the provisional restoration 914 can be fabricated on the articulator to preserve the incisal guide path G.

In some embodiments, the incisal guide model 910 is fabricated using the rapid fabrication machine 126 based on the incisal guide data 906. In some embodiments, the provisional design system 902 generates the incisal guide data 906 from the digital dental model 120. In other embodiments, the provisional design system 902 generates the incisal guide data 906 by moving the lower arch along the paths defined in the motion data. In some embodiments, the incisal guide data 906 is generated by sweeping the lower arch model data through all of the bite positions recorded in the functional bite map data 121 or the motion data 112. Additionally, in some embodiments, the incisal guide data 906 is generated from a pre-preparation impression of the lingual surface of the upper arch of the patient P. In some embodiments, the incisal guide data 906 is formed by inverting the lingual surface of the upper arch of the patient P. Similarly, in some embodiments, the incisal guide data 906 is formed by inverting the surface formed by sweeping the lower arch model through all of the bite positions and paths. In this manner, the incisal guide model 910 forms a surface that causes motion on the articulator that mimics the motion captured from the patient. Other embodiments are possible as well.

In some embodiments, the incisal guide model 910 includes one or more retention structures 1224 and 1226. The retention structures 1224 and 1226 are configured to align and secure the incisal guide model 910 to the articulator 1200.

In the example shown, the retention structure 1224 comprises a peg that is configured to fit in a corresponding hole in the incisal guide model mounting plate 1212. In some embodiments, the retention structure 1224 includes a registration grove or ridge to properly align the incisal guide model 910 to the incisal guide model mounting plate 1212. In the example shown, the retention structure 1226 comprises a clip that is configured to fit around the edge of the incisal guide model mounting plate 1212.

In some embodiments, the retention structures 1224 and 1226 are included in the incisal guide data. Additionally, some embodiments include more, fewer, or different retention structures.

Alternatively, in some embodiments, the articulator 1200 is fabricated using one or more rapid fabrication machines. In some embodiment, in addition to or instead of the incisal guide model 910, the socket 1208 is formed to cause the upper arch dental model 1220 to move relative to the lower arch dental model 1214 in a manner that is similar to the actual motion of the patient P's jaw (e.g., based on the motion data 112).

Figure 33:
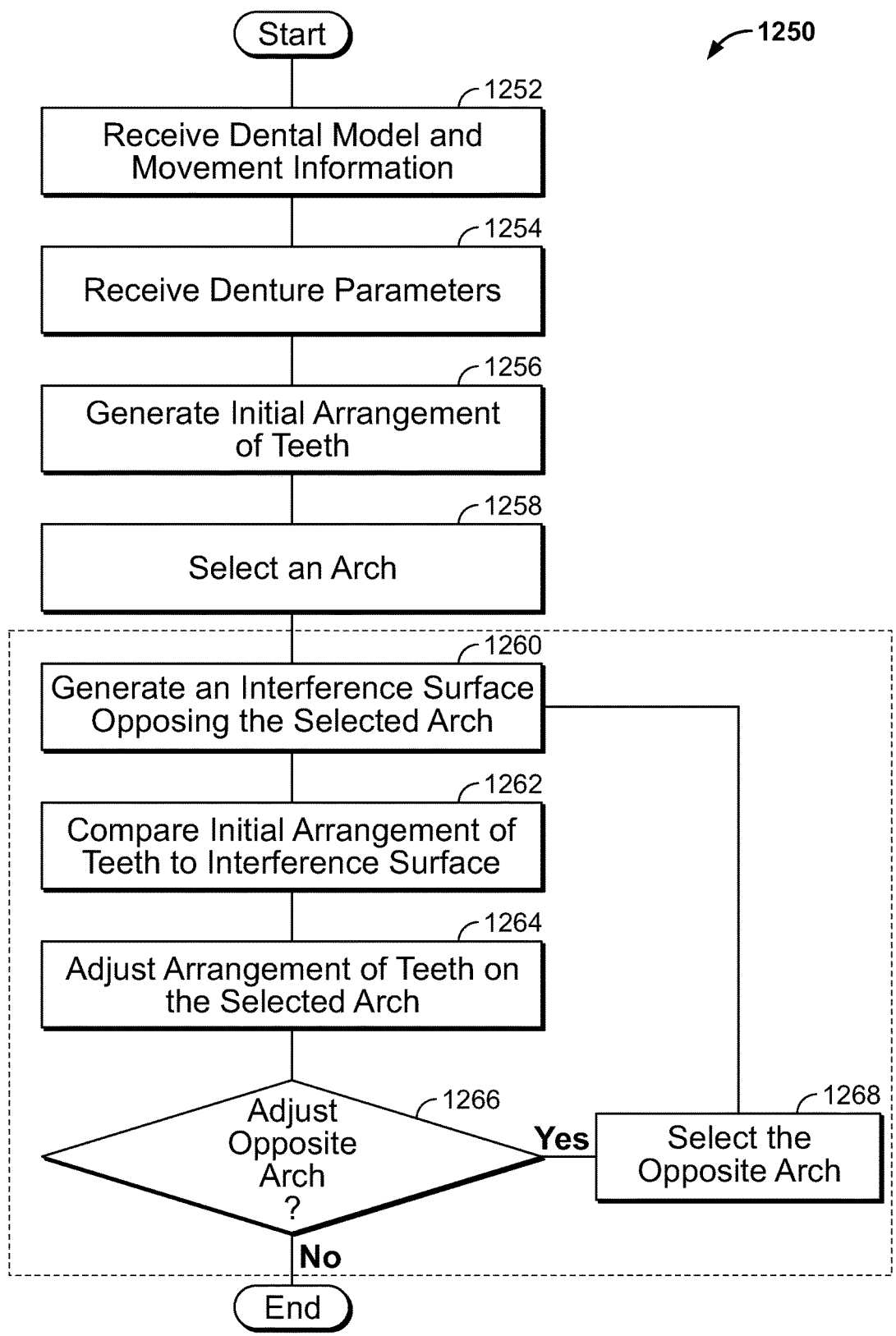
FIG. 33 is a flow chart illustrating an example method of using the system of FIG. 1 to fabricate a denture dental restoration.

FIG. 33 is a flow chart illustrating an example method 1250 of using the system 100 to fabricate a denture dental restoration. In some embodiments, the method 1250 is performed in the dental office 102. In other embodiments, the method 1250 is performed in multiple locations, such as one or more dental offices and dental laboratories. In some embodiments, the method 1250 is performed by the interference modeling engine 450 and the restoration design engine 452 using a processor (such as processing device 180, shown in FIG. 2). In this example, the method 1250 includes operations 1252, 1254, 1256, 1258, 1260, 1262, 1264, 1266, and 1268. The method 1250 may be used to generate partial or complete dentures for one or both arches.

At operation 1252, the digital dental model 120 and movement information are received. In some embodiments, the digital dental model 120 is generated from a dental impression 108 of an edentulous region of the patient P's dentition. In some embodiments, the operation 1252 is similar to the operation 492 (which is illustrated and described with respect to at least FIG. 12).

At operation 1254, denture parameters are received. Non-limiting examples of denture parameters include a vertical dimension, a location of the center line, an occlusal plane height, and a tooth style. In some embodiments, the parameters are received with the digital dental model 120 (e.g., the parameters are specified by the dentist D). In other embodiments, the parameters may be received from a user input received through a user interface. Alternatively, the parameters may be retrieved from a database. Additionally, in some embodiments, at least some of the parameters are received by loading default values (which may be based on measured parameters of the digital dental model 120 or other parameters (e.g., patient age, gender, height, etc.)).

At operation 1256, an initial arrangement of the denture teeth is generated based on the digital dental model 120 and the received denture parameters. The initial arrangement may be generated automatically by the design system 118 using templates of denture teeth arrangements, rules for arranging denture teeth, or both. Alternatively or additionally, in some embodiments, a user arranges the denture teeth by interacting with the design system 118 through a user interface.

At operation 1258, an arch is selected. At operation 1260, an interference surface opposing the selected arch is generated. In some embodiments, the interference surface is generated by sweeping the initial arrangement of teeth (or dentition from the digital dental model 120 when the denture is being fabricated for a single arch) opposing the selected arch according to the received movement information. In some embodiments, the interference surface is generated in a manner similar to that illustrated and described with respect to FIG. 13.

At operation 1262, the interference surface is compared to the initial arrangement of teeth on the selected arch. In some embodiments, a color map is generated to show interferences between the initial arrangement of teeth and the interference surface.

At operation 1264, the teeth in the selected arch can be adjusted or repositioned based on interferences identified using the interference surface. In some embodiments, the teeth are adjusted or repositioned automatically. Additionally, in some embodiments, a user may input commands to adjust or reposition the teeth. In some embodiments, the teeth may be adjusted or repositioned to fully eliminate interferences. In other embodiments, the interferences are partially eliminated. For example, in some embodiments where complete dentures for both arches are being fabricated, some of the interferences may be addressed by adjusting or repositioning teeth on the opposing arch.

At operation 1266, it is determined whether to adjust the opposing arch. If a denture is being fabricated for a single arch, it will not be possible to adjust the opposing arch and the method will end. Alternatively, if denture dental restorations are being fabricated for both arches and interferences exist, the method may proceed (automatically or based on user input) to operation 1268, where the opposite arch is selected for generation. After operation 1268, the method proceeds back to operation 1260 where an interference surface is generated and the rest of the method 1250 can be repeated to adjust the opposite arch. In some embodiments, the method 1250 iterates between adjusting the arches multiple times to eliminate or minimize interferences.

After method 1250 is complete, the designed dentures may be fabricated using various techniques. For example, the denture dental restoration may be fabricated in part or in whole using one or more rapid fabrication machines according to techniques described elsewhere herein. Additionally, in some embodiments, molds or other tools that can be used to fabricate the denture dental restoration are formed using one ore more rapid fabrication machines.

FIG. 34 illustrates an embodiment of a fiducial device 1290 that can be secured to a portion of the dentition of the patient P for use in generating the motion data 112. The fiducial device 1290 includes an exterior surface 1292 and an interior surface 1294.

In some embodiments, the exterior surface 1292 is configured so that the location of the fiducial device 1290 can be determined from an image that includes at least a portion of the exterior surface 1292. In some embodiments, the fiducial device 1290 is formed in a predetermined size and shape. For example, in some embodiments, the exterior surface is a portion of the surface of a sphere (such as a hemisphere). In some embodiments, the exterior surface is sized to fit on a single tooth. For example, in some embodiments, the exterior surface is a portion of a sphere having a diameter of between 3 and 9 mm. Beneficially, when the fiducial device 1290 includes a partially spherical surface of a known dimension, the location of the center of the sphere can be determined by fitting a sphere (or circle) to the portion of the sphere in the captured image.

In some embodiments, the interior surface 1294 is formed to fit a typical contour of the patient P's dentition. In some embodiments, the interior surface 1294 is designed to fit the contour of a particular type of tooth (e.g., anterior, incisor, cuspid, molar, etc.). In some embodiments, the interior surface 1294 is coated with an adhesive or bonding agent that operates to temporarily secure the fiducial device 1290 to the dentition of the patient P.

Additionally, in some embodiments, the fiducial devices include a clasp or clip for coupling to a portion of the patient P's dentition. Additionally, one or more of the fiducial devices 1290 may be coupled to a tray or clench that is configured to couple to the dentition of the patient P. Furthermore, the tray or clench may include extensions that are intraoral or extraoral and upon which the fiducial devices 1290 are disposed.

Figure 35:
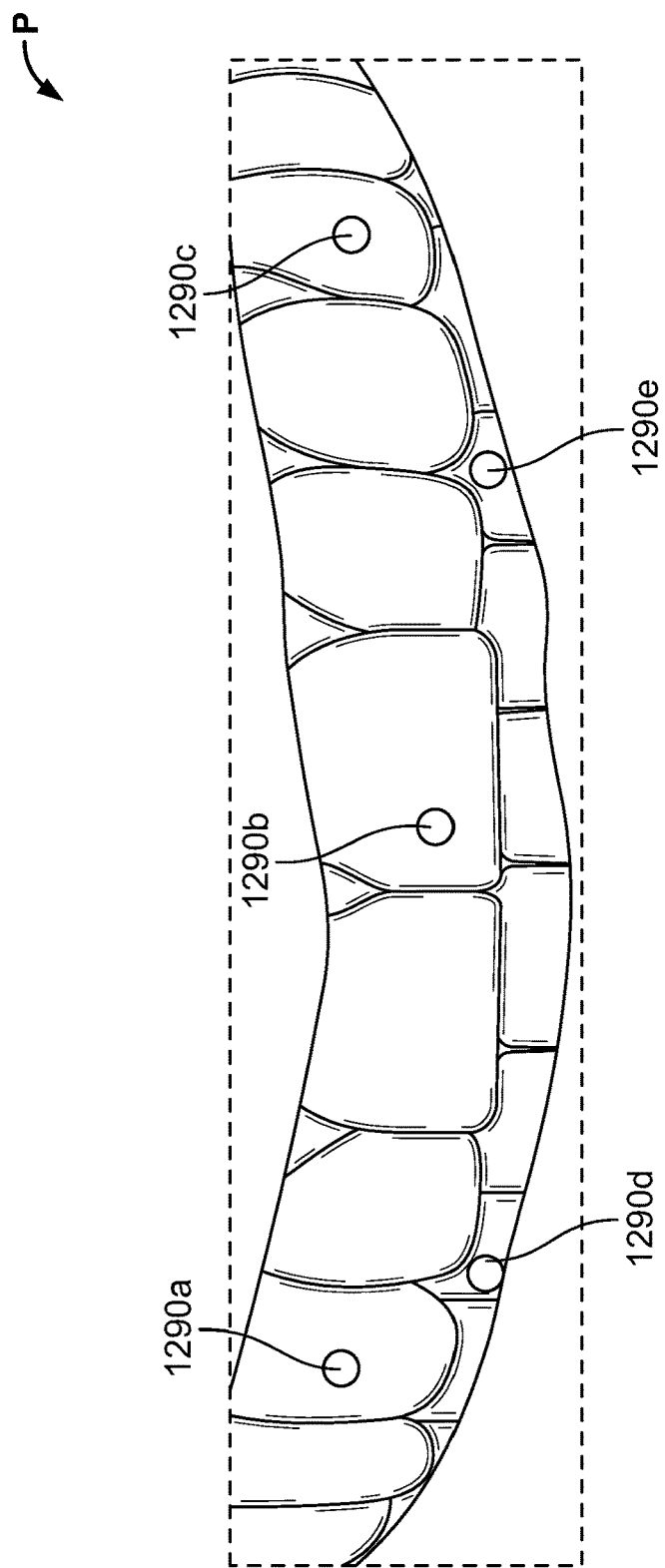
FIG. 35 is an illustration of an example of a plurality of the fiducial devices of FIG. 34 coupled to the dentition of the patient.

FIG. 35 is an illustration of an example of a plurality of the fiducial devices 1290 coupled to the dentition of the patient P. In this example, the fiducial devices 1290a, 1290b, and 1290c are coupled to various points of the upper dentition of the patient P. Also in this example, the fiducial devices 1290d and 1290e are couple to various points of the lower dentition of the patient P. In other embodiments, fiducial devices 1290 are attached to additional, fewer, or different locations on the dentition of the patient P.

In some embodiments, images or videos of the dentition of the patient P are captured while the fiducial devices 1290 are coupled to the patient's dentition. These images or videos can then be processed to determine first the locations of the fiducial devices 1290 and then the location and orientation of the patient P's upper dentition relative to the patient P's lower dentition.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A method of generating a dental restoration for a patient, the method comprising:
   generating dental restoration model data representing a dental restoration surface;
   generating an interference surface from an impression representing at least a portion of a dentition of the patient and motion data representing a plurality of bite positions of the dentition of the patient, wherein the interference surface is generated using at least two of the plurality of bite positions of the dentition of the patient;
   determining that the plurality of bite positions represents a full bite path of the dentition;
   calculating a distance between the dental restoration surface and the interference surface;
   assigning colors to regions of the dental restoration surface, based on the calculated distance;
   generating a design of the dental restoration for a dental restoration site in the patient's dentition, using the interference surface; and
   generating the dental restoration from the design of the dental restoration.

2. The method of claim 1, wherein the dental restoration site comprises an edentulous space.

3. The method of claim 2, wherein the edentulous space comprises a complete arch.

4. The method of claim 1, further comprising:
   receiving a first image of the dentition of the patient, wherein the first image is captured with the dentition of the patient in a first position, the first image including a fiducial;
   receiving a second image of the dentition of the patient, wherein the second image is captured with the dentition of the patient in a second position, the second image including the fiducial;
   determining a first position of the fiducial based on the first image;
   determining a second position of the fiducial based on the second image; and
   generating the motion data based on interpolating between the first position and the second position.

5. The method of claim 4, wherein the fiducial comprises:
   an exterior surface shaped as a portion of a sphere; and
   an interior surface contoured to fit a tooth.

6. The method of claim 5, wherein the interior surface includes an adhesive agent.

7. The method of claim 1, wherein the denture dental restoration is generated using a rapid fabrication machine.

* * * * *